US009193682B2

(12) United States Patent
Fenoli et al.

(10) Patent No.: US 9,193,682 B2
(45) Date of Patent: Nov. 24, 2015

(54) SYNTHESIS OF TRITHIOCARBONATES AND ALLYL SULFIDES AND THEIR APPLICATION INTO ADVANCES IN COVALENT ADAPTABLE NETWORKS

(71) Applicants: Christopher R Fenoli, Riviera Beach, FL (US); Christopher N Bowman, Boulder, CO (US)

(72) Inventors: Christopher R Fenoli, Riviera Beach, FL (US); Christopher N Bowman, Boulder, CO (US)

(73) Assignee: Christopher R. Fenoli, Riviera Beach, FL (US)

( * ) Notice: Subject to any disclaimer, the term of this patent is extended or adjusted under 35 U.S.C. 154(b) by 6 days.

(21) Appl. No.: 14/246,518

(22) Filed: Apr. 7, 2014

(65) Prior Publication Data

US 2014/0303391 A1    Oct. 9, 2014

Related U.S. Application Data

(60) Provisional application No. 61/809,245, filed on Apr. 5, 2013.

(51) Int. Cl.
| | | |
|---|---|---|
| *C07F 7/04* | (2006.01) | |
| *C07C 329/00* | (2006.01) | |
| *C07C 323/18* | (2006.01) | |
| *C07C 323/20* | (2006.01) | |

(52) U.S. Cl.
CPC ............. *C07C 329/00* (2013.01); *C07C 323/18* (2013.01); *C07C 323/20* (2013.01)

(58) Field of Classification Search
CPC .................................................. C07C 329/00
USPC ........................................................ 556/429
See application file for complete search history.

(56) References Cited

PUBLICATIONS

Ting et al., Biomacromolecules (2009), 10(2), 342-352.*
Aoyagi, Naoto, Functional RAFT Agents for Radical-Controlled Polymerization: Quantitative Synthesis of Trithiocarbonates Containing Functional Groups as RAFT Agents Using Equivalent Amount of CS2. Japan, Journal of Polymer Science: Part A: Poymer Chemistry, vol. 47, 3702-3709 (2009) Wiley Periodicals, Inc.
Aoyagi, Naoto, Mild and Efficient One-Step Synthesis of Trithiocarbonates Using Minimum Amount of CS2. University of Colorado System No. 4, 636-638 (2006) Georg Thieme Verlag Stuttgart.
Barner, Leonie, Complex Macromolecular Architectures by Reversible Addition Fragmentation Chain Transfer Chemistry: Theory and Practice. Macromal Rapid Commun. vol. 28, 539-559 (2007) Macromomelcular Journals.
Barton, Derek, Carbethoxyallylation Using Radical Chemistry. Tetrahedrom Letters, vol. 25 2787-2790 (1984) Pergamon Press Ltd.
Braga, Roberto, Factors involved in the development of polymerization shrinkage stress in resin-composites: A systematic review. Dental Materials vol. 21 962-970 (2005) Elsevier Ltd.
Capperucci, Antonella, Thiophilic Allylation of Dithioesters and Trithiocarbonates. Great Britain, Tetrahedron Letters, vol. 35 No. 1 161-164 (1994) Pergamon Press Ltd.
Chaturvedi, Devdutt, An Efficient, One-pot synthesis of trithiocarbonates from the corresponding thiols using the Mitsunobu reagent. Tetrahedron Letters vol. 49 4886-4888 (2008) Elsevier Ltd.
Chiefari, John, Living Free-Radical Polymerization by Reversible Addition—Fragmentation Chain Transfer: The RAFT Process. Australia, Macromolecules vol. 31 5559-5562 (1998) American Chemical Society Publications.
Chiefari, John, Thiocarbonylthio Compounds (S=C(Z)S-R) in Free Radical Polymerization with Reversible Addition-Fragmentation Chain Transfer (RAFT Polymerization). Effect of the Activating Group Z. Macromolecules vol. 36 2273-2283 (2003) American Chemical Society Publications.
Cook, Wayne, Effect of Cross-Link Density on Photoplasticity of Epoxide Networks Containing Allylic Dithioether Moieties. Macromolecules vol. 45, 9734-9741 (2012) American Chemical Society Publications.
Davidson, C.L., Polymerization shrinkage and polymerization shrinkage stress in polymer-based restoratives. Great Britain, Journal of Dentistry vol. 25 No. 6, 134-140 (1997) Elsevier Ltd.
Fenoli, Christopher, Synthesis of novel trithiocarbonate and allyl sulfide containing monomers, The Royal Society of Chemistry (2013).
Godt, H.C. Jr. The Synthesis of Organic Trithiocarbonates, The Research Department of the Organic Chemicals Division, Monsanto Chemical Co. 4047-4051 (1961).
Kiasat, Ali Reza, A Novel One-step Synthesis of Symmetrical Dialkyl Trithiocarbonates in the Presence of Phase-Transfer Catalysis, Journal of the Chinese Chemical Society vol. 55 639-642 (2008).
Kloxin, Christopher, Mechanophotopatterning on a Phtoresponsive Elastomer, Advanced Materials vol. 23 1977-1981 (2011) Verlag GmbH & Company KGaA.
Kloxin, Christopher, Stress Relaxation via Addition—Fragmentation Chain Transfer in a Thiol-ene Photopolymerization, Macromolecules vol. 42 2551-2556 (2009) American Chemical Society Publications.
Lai, John T., Functional Polymers from Bovel Carboxyl-Terminated Triothiocarbonates as Highly Efficient RAFT Agents, Macromolecules vol. 35 6754-6756 (2002) American Chemical Society Publications.
Lee, Awm, One Pot Phase Transfer Synthesis of Trithiocarbonates from Carbon Disulphide adn Alkyl Halides, Synthetic Communications vol. 18 1531-1536 (1988) University of Colorado at Boulder Libraries.
Leung, Diana, Reducing Shrinkage Stress of Dimethacrylate Networks by Reversible Addition—Fragmentation Chain Transfer, Macromolecular Chemistry and Physics vol. 213 198-204 (2012) Verlag GmbH & Company.

(Continued)

*Primary Examiner* — Porfirio Nazario Gonzalez
*Assistant Examiner* — Kofi Adzamli
(74) *Attorney, Agent, or Firm* — Mark Terry

(57) ABSTRACT

Monomers having a C-B-A-B-C structure are disclosed, where A is a core of either trithiocarbonate and allyl sulfide, where B are linker units, and where C are end units. The end units may comprise acrylates, methacrylates, alcohol(s), amine(s), and alkynes, among others. The linker units may include an alkane, alkene, phenyl, diphenyl, or benzylic group, among others. Methods of synthesizing such compounds are also disclosed.

8 Claims, 29 Drawing Sheets

(56) References Cited

PUBLICATIONS

Meijs, Gordon F., Chain Transfer by an Addition-Fragmentation Mechanism the Use of a-benzloxystyrene for the preparation of low-molecular-weight poly(methyl methacrylate) and polystyrene, Makromolekulare Chemistry Rapid Communication vol. 9 547-551 (1988) Interlibrary Loans, Colorado State.

Meijs, Gordon F., Preparation of Controlled Molecular Weight, Olefin-Terminated Polymers by Free Radical Methods. Chain Transfer USing Allylic Sulfides, Macromolecules vol. 21 3122-3124 (1988) American Chemical Society Publications.

Moad, Graeme, Living Radical Polymerization by the RAFT Process—A Second Update, Australia, J. Chem. vol. 62 1402-1472 (2009) CSIRO Publishing.

Moad, Graeme, Radical Addition—Fragmentation Chemistry in Polymer Synthesis, Australia, Polymer vol. 49 1079-1131 (2008) CSIRO Molecular and Health Technologies.

Nicolay, Renaud, Responsive Gels Based on a Dynamic Covalent Trithiocarbonate Cross-Linker, Macromolecules vol. 43 4355-4361 (2010) American Chemical Society Publications.

Park, Hee Young, Covalent Adaptable Networks as Dental Restorative Resins: Stress Relaxation by Addition-Fragmentation Chain Transfer in Allyl Sulfide-Containing Resins, Academy of Dental Materials vol. 26 1010-1016 (2010) Elsevier Ltd.

Park, Hee Young, Stress Relaxation by Addition-Fragmentation Chain Transfer in Highly Cross-Linked Thiol-Yne Networks, Macromolecules vol. 43 10188-10190 (2010) American Chemical Society.

Park, Hee Young, Stress Relaxation by Addition-Fragmentation Chain Transfer in High Tg, High Conversion Methacrylate-Based Systems, Macromolecules vol. 45 5640-5646 (2012) American Chemical Society.

Perrier, Sebastien, Reversible Addition-Fragmentation Chain Transfer Polymerization Mediated by a Solid Supported Chain Transfer Agent, Macromolecules vol. 38 6770-6774 (2005) American Chemical Society.

Scott Timothy F., Photoinduced Plasticity in Cross-Linked Polymers, Science vol. 308 1615-1617 (2005) ProQuest Biology Journals.

Sugawara, Akira, One-Pot Synthesis of Alkyl Aryl Trithiocarbonates from Benzenethio;s, Alkyl Halides, and Carbon Disulfide with a Phase-transfer Catalyst, Japan, The Chemical Society of Japan vol. 57 3353-3354 (1984).

Wydra, James W. Influence of Small Amounts of Addition-Fragmentation Capable Monomers on Polymerization-Induced Shrinkage Stress, Journal of Polymer Science, Part A: Polymer Chemistry 1-7 (2014) Wiley Periodicals, Inc.

* cited by examiner

General Structure: C – B – A – B – C

Alkyl:

Alkene

Benzyl

Phenyl

Diphenyl

Acrylate

Scheme 4: Synthesis of Allyl Sulfide Agents

Reagents and Conditions: a. Sodium methoxide in MeOH, 3-chloro-2-chloromethyl-1-propene, 16hrs, Δ b. Acryloyl chloride, Et₃N, 0°C to 25°C.

SYNTHESIS OF TRITHIOCARBONATES AND ALLYL SULFIDES AND THEIR APPLICATION INTO ADVANCES IN COVALENT ADAPTABLE NETWORKS

CROSS-REFERENCE TO RELATED APPLICATION

This patent application claims priority under 35 U.S.C. §119 to U.S. Provisional Patent Application No. 61/809,245, filed Apr. 5, 2013, which is incorporated herein by reference in its entirety.

BACKGROUND

The RAFT (Reversible addition-fragmentation termination) process has rapidly become one of the two most dominant controlled radical polymerization processes and is ubiquitous in commercial and research practice. The RAFT process involves a radical, typically generated either thermally or by light exposure, attacking a double bond to form a tri-centered radical intermediate (I). This intermediate, which is generally unreactive to further addition to double bonds, then cleaves (i.e., fragments) in one of three possible manners, leaving a newly formed double bond (I) and another radical species to further the RAFT process (I), as illustrated in FIG. 1.

SUMMARY

The ability to synthesize a variety of functionalized RAFT and addition-fragmentation chain transfer (AFCT) monomers capable of being incorporated into a polymer network is appealing for numerous photochemical network modification strategies. By incorporating RAFT and AFCT monomers into polymer networks, the addition fragmentation chain transfer process enables covalent bonds to be broken and reformed throughout the network. There are a number of important applications and benefits for the type of network rearrangement implemented in photochemical photoresponsive polymer networks (PRPN's) or covalent adaptable networks (CAN's) for example control of shrinkage stress in acrylate polymerizations, mechanopatterning, adhesion, and lithography, among others.

In one aspect, the invention provides monomers that exhibit controlled reversible addition-fragmentation termination (CRAFT monomers). The CRAFT synthons may be described by the general structure illustrated in FIG. 2, having units A, B, and C, and having the structure C-B-A-B-C. In an embodiment, the synthons consist of a RAFT core unit (A) that is either an allyl sulfide or trithiocarbonate moiety. The linker unit (B) is synthetically connected to the RAFT core (A) and capped with an end group (unit) (C). Thus, the structure generally comprises a core unit (A), two linker units (B) each connected to different portions of the core unit (A), and two end units (C) each connected to ends of respective ones of the linker units (B). The linkers (linker units) included into the RAFT monomers may be chosen to elicit specific structure-property relationships (e.g., mechanical properties) into the final CAN's. Tailored at the ends of the CRAFT monomers are (C) segments that may consist of a (meth)acrylate subunit, or other end units (C), described below. The CRAFT monomers can undergo photoinitiated radical polymerization, thiol-(meth)acrylate radical polymerization, and/or base or nucleophile-catalyzed thiol-Michael addition polymerizations, as appropriate. This approach facilitates a wide range of spatial control, temporal control, spatio-temporal control, and overall polymer property behavior control in the network.

In one aspect, the invention provides allyl sulfide monomers comprising an allyl sulfide core unit (A) and acrylate or methacrylate end groups (C). The linking moiety, B, may comprise any appropriate group or molecule that is capable of connecting the allyl sulfide group (A) with the end group (C). As shown by, for example, Table 1, below, and FIGS. 17-20, the linker unit B may comprise (or consist of) a first portion and a second portion. In this approach, the first portion of B may have a first end connected to the core unit A. In this approach, the second portion of B is an oxygen atom, and this oxygen atom is connected to the second (other) end of the first portion. In some embodiments, the first portion of B may comprise a single alkylene group or a multiple alkylene chain. i.e., $(-CH_2-)_n$ and may be linear or branched. The first portion of B may also comprise one or more carbon-carbon double bonds. In other embodiments, the first portion of B may comprise an aromatic group or multiple aromatic groups. In an embodiment, the first portion of the linker unit B may comprise a C1-C10 or a C2-C4 alkene, i.e., $(-CH_2-)_n$. In an embodiment, the first portion of the linker unit B may comprise a C2-C10 or a C3-C5 alkenylene. In other embodiments, the first portion of B may comprise a phenylene or di-phenylene. The first portion of B may also comprise $(-CH_2-)_n$ where one or more of $(CH_2)$ are replaced with phenylene. In one embodiment, the first portion of B may comprise a C3-C10 alkane (branched or unbranched). In one embodiment, the first portion of B may comprise a branched C2-C10 alkane, where one or more of the $(CH_2)$ branches of the alkane are replaced by various electron-withdrawing groups (EWG's) including, for example, cyano (CN), nitro ($NO_2$), trihalides, carboxylic acids, sulfonates, esters, ketones, and aldehydes. In one embodiment, the first portion of B may comprise a C2-C10 alkene (branched or unbranched, and cis or trans). In one embodiment, the first portion of B may comprise a C2-C10 alkyne. In one embodiment, the first portion of B may comprise one or more aromatic rings. In one embodiment, the first portion of B may include a C2 or higher alkane, such as the alkane shown in FIG. 15a. In one embodiment, the first portion of B may include a C3 or higher alkene, such as the alkene shown in FIG. 15b. In one embodiment, the first portion of B may include a benzyl group, such as the benzyl group shown in FIG. 15c. In one embodiment, the first portion of B may include a phenyl group, such as the phenyl group shown in FIG. 15d. In one embodiment, the first portion of B may include a diphenyl group, such as the diphenyl shown in FIG. 15e. As noted above, in some embodiments, the end subunit (C) connects to the oxygen atom of the linker unit B. In one embodiment, C is an acrylate, such as the acrylate shown in FIG. 16. In another embodiment, C is a methacrylate. In yet another embodiment, C may be hydrogen, thereby forming an alcohol (OH).

In another aspect, the invention provides trithiocarbonate monomers comprising a trithiocarbonate core unit (A) and (meth)acrylic end groups (C). The linking moiety (linker unit), B, may comprise any appropriate group or molecule that is capable of connecting the trithiocarbonate with the end group. As shown by, for example, Table 1, below, and FIGS. 17-20, the linker unit B may comprise (or consist of) a first portion and a second portion. In this approach, the first portion of B may have a first end connected to the core unit A. In this approach, The second portion of B is an oxygen atom, and this oxygen atom is connected to the second (other) end of the first portion. The first portion of B may comprise a single alkylene group or a multiple alkylene chain. i.e., $(-CH_2-)_n$ and may be linear or branched. The first portion of B may also comprise one or more carbon-carbon double bonds. In other embodiments, the first portion of B may comprise an aromatic group or multiple aromatic groups. In an embodiment, the first portion of the linker unit B is C1-C10, or C2-C4 alkene i.e., (—CH$_2$—)$_n$. In an embodiment, the first portion of the linker unit B is C2-C10 or C3-C5 alkenylene. In an embodiment, the first portion of the linker unit B is C2-C10 or C3-C5 alkenylene (comprising at least one carbon-carbon double bond). In other embodiments, the first portion of B may be phenylene or di-phenylene. The first portion of B may also be (—CH$_2$—)$_n$ where one or more of (CH$_2$) are replaced with phenylene. In one embodiment, the first portion of B is a C2-C10 alkane (branched or unbranched). In one embodiment, the first portion of B may comprise a branched C2-C10 alkane, where one or more of the (CH$_2$) branches of the alkane are replaced by various electron-withdrawing groups (EWG's) including, for example, cyano (CN), nitro (NO$_2$), trihalides, carboxylic acids, sulfonates, esters, ketones, and aldehydes. In one embodiment, the first portion of B is a C2-C10 alkene (branched or unbranched, and cis or trans). In one embodiment, the first portion of B is a C2-C10 alkyne. In one embodiment, the first portion of B is an aromatic ring. In one embodiment, the first portion of B may include an C2 or higher alkane, such as the alkane shown in FIG. 15*a*. In one embodiment, the first portion of B may include a C3 or higher alkene, such as the alkene shown in FIG. 15*b*. In one embodiment, the first portion of B may include a benzylic group, such as the benzylic group shown in FIG. 15*c*. In one embodiment, the first portion of B may include a phenyl group, such as the phenyl group shown in FIG. 15*d*. In one embodiment, the first portion of B may include a diphenyl group, such as the diphenyl group shown in FIG. 15*e*. As noted above, in some embodiments, the end subunit (C) connects to the oxygen atom of the linker unit B. In one embodiment, C is an acrylate, such as the acrylate shown in FIG. 16. In another embodiment, C is a methacrylate. In yet another embodiment, C may be hydrogen, thereby forming an alcohol (OH). Any of the above-described monomers may be polymerized (e.g., with an appropriate mixture, described below) to form a covalently adaptable network.

In another aspect, the invention provides methods for synthesizing allyl sulfide monomers and trithiocarbonate monomers with meth(acrylic) end groups. In some embodiments, the reactions may be carried out at mild temperatures (e.g., ambient to about 100° C., such as from ambient to about 60° C., such as from ambient to about 40° C.) without the use of excess, costly, or toxic reagents (e.g., in the absence of NaOH (50% wt.), thiophosgene, chlorodithioformates, and Grignard reagents, to name a few). The use of such mild conditions, as described below (e.g., implementing stoichiometric carbon disulfide, a mild base (potassium carbonate, sodium carbonate, or cesium carbonate) in a general polar aprotic solvent), allows for the chemistry to be carried out in atmospheric conditions in the presence of oxygen and moisture. Additionally, after the formation of the AFT (addition-fragmentation chain transfer) core, the subsequent synthetic manipulations may occur using mild techniques (e.g., using acid chloride functional groups or Mitsunobu reactions) to incorporate the (meth)acrylate capped monomers without degrading the AFT core.

In an embodiment, the synthetic strategy for the trithiocarbonate monomers involves building a trithiocarbonate backbone with protected oxygen atoms at both ends, then deprotection of the oxygen atom and addition of the (meth)acrylate end groups. In an embodiment, the reaction to build the trithiocarbonate backbone involves the use of a mild base, such as potassium carbonate, coupled with polar aprotic solvents using stoichiometric carbon disulfide with alcohol functionalized alkyl halides. In an embodiment, the synthesis uses the reaction of carbon disulfide and potassium carbonate in a polar aprotic solvent with an alkyl halide, a vinyl halide or a benzylic halide, which contain an oxygen atom protected by a silyl protecting group at one end (see, FIG. 17, Scheme 1). The silyl protecting group may be TBS (tert-butyl dimethyl silyl ether), or other suitable silyl protecting group. In an embodiment, the oxygen atom is subsequently deprotected using tetrabutyl ammonium fluoride (TBAF)/AcOH, which allows the use of fluorine to deprotect the silyl group without allylation of the AFT core by TBAF. The deprotection may be followed by a Mitsunobu coupling to add the (meth)acrylate end groups (see, FIG. 18, Scheme 2).

When producing trithiocarbonate monomers having end units of acrylates or methacrylates, a method may include reacting carbon disulfide (CS$_2$) in the presence of one of (a) a halogenated carbon-compound, or (b) a salt or ester of a sulfonic acid. In one embodiment, the halogenated carbon-compound is selected from the group consisting of an alkyl halide, a vinyl halide and a benzylic halide. In one embodiment, the sulfonic acid is selected from the group consisting of mesylates, tosylates, nosylates, and brosylates. In one embodiment, an oxygen atom is connected to an end of the halogenated carbon-compound or the salt or ester of the sulfonic acid. Due to the reacting step, reaction products may be formed, wherein the reaction products at least include first products, wherein the first products are a compound comprising a trithiocarbonate core unit (A) and two linker units (B). Each of the two linker units may comprise a first portion and a second portion, wherein each of the two linker units are connected to the core unit via the first portion. The first portion may be selected from the group consisting of an alkane, an alkene, and a benzylic group. The second portion comprises an oxygen atom connected to the first portion and a silyl protecting group connected to the oxygen atom. In one embodiment, the method may include removing the silyl protecting group, thereby creating an intermediate product. The method may include connecting an end unit (C) to each of the oxygen atoms of the linker units of the intermediate product, thereby producing second products (e.g., the monomer), wherein the end unit is selected from the group consisting of hydrogen, an acrylate and a methacrylate.

When producing trithiocarbonate monomers having end units of acrylates or methacrylates, the step of reacting carbon disulfide may include completing the reacting in a polar aprotic solvent at a temperature of from 10° to 100° C. Generally, stoichiometric amounts of carbon disulfide are present so as to restrict formation of excess by-products. In one embodiment, the reacting step occurs at a temperature of from 10° to 80° C. In one embodiment, reacting step occurs at a temperature of from 10° to 60° C. In one embodiment, reacting step occurs at a temperature of from 10° to 40° C. In one embodiment, the reacting step occurs at a temperature of at least ambient.

When producing trithiocarbonate monomers having end units of acrylates or methacrylates, the step of reacting carbon disulfide may produce reaction products, the reaction products including the monomer as the first products. In one embodiment, the reaction products comprise at least 90% (mol.) of the first product (i.e., a yield of at least 90%). In one embodiment, the reaction products comprise at least 92% (mol.) of the first product. In one embodiment, the reaction products comprise at least 94% (mol.) of the first product. In one embodiment, the reaction products comprise at least 96% (mol.) of the first product. In one embodiment, the reaction products comprise at least 98% (mol.) of the first product. In one embodiment, the reaction products comprise at least 99% (mol.) of the first product.

When producing trithiocarbonate monomers having end units of acrylates or methacrylates, the step of removing the silyl protecting group may comprise contacting the first product with a removing agent solution, thereby producing an intermediate product, and this contacting may occur at a temperature of from 248° K to 313° K (−25° C. to 40° C.). In one embodiment, the contacting occurs at a temperature of from 258° K to 303° K. In one embodiment, the contacting occurs at a temperature of from 268° K to 293° K. In one embodiment, the contacting occurs at a temperature of from 270° K to 280° K. The removing agent solution generally comprises tetrabutyl ammonium fluoride (TBAF) and an acid. This acid may have a $pK_a$ of from 3.0 to 6.5. In one embodiment, this acid may have a $pK_a$ of from 4.5 to 6.0. In one embodiment, the acid is acetic acid. In one embodiment, the acid is phosphoric acid. In one embodiment, the acid is citric acid.

When producing trithiocarbonate monomers having end units of acrylates or methacrylates, after the removing the silyl protecting group step to produce the intermediate product, the connecting step may comprises dissolving the intermediate product in solution, and then adding one of diethyl azodicarboxylate (DEAD) or diisopropyl azodicarboxylate (DIAD) to the solution, thereby producing a second product (e.g., the monomer). In one embodiment, the solution comprises at least one of acrylic acid and methacrylic acid (depending on the desired end unit), and a coupling agent. In one embodiment, the connecting step comprises producing by-products. The second products plus the by-products equals a mixture, and wherein the mixture comprises at least 33% of the second products (i.e., a yield of at least 33%). In one embodiment, the mixture comprises at least 50% of the second products. In one embodiment, the mixture comprises at least 75% of the second products. In one embodiment, the mixture comprises at least 85% of the second products. In one embodiment, the mixture comprises at least 90% of the second products. In one embodiment, the mixture comprises at least 95% of the second products. In one embodiment, the mixture comprises at least 99% of the second products.

In an embodiment, the allyl sulfide monomers are synthesized by formation of a core allyl disulfide scaffold with alcohol groups at both ends followed by addition of acrylate or methacrylate to the pendant alcohol groups. In an embodiment, the core allyl disulfide scaffold is formed by reaction of two equivalents of a thio-alcohol with one equivalent of 3-chloro-2-chloromethyl-1 propene in a solution of sodium methoxide. Suitable thio-alcohols include, for example, mercaptoethanol, thiophenol, and 4-hydroxyl-4'-mercaptobiphenyl. The 4-hydroxyl-4'-mercaptobiphenyl may be synthesized from 4-iodoanisol and 4-bromothioanisol via a Kumada coupling. The product may be subsequently reduced with sodium ethanethiolate to yield 4-hydroxyl-4'-mercaptobiphenyl (see, FIG. 19, Scheme 3). The acrylate or methacrylate may be added to the pendent alcohol using modified Schotten-Baumann conditions, where the acyl chloride is reacted with the alcohol using triethylamine as an acid scavenger (see, FIG. 20, Scheme 4). The acid chloride reaction to produce the diester acrylate functionality may be useful because the ease of the reaction conditions and the cost of acryloyl chloride. The reaction may be completed using Mitsunobu conditions, as well. The Mitsunobu reaction may provide overall better yields, but the purification of the final product may be difficult (e.g., when the DEAD and triphenylphosphine bi-products are hard to separate from the final product).

In another aspect, the invention provides trithiocarbonate monomers comprising a trithiocarbonate core unit (A) with amines at the ends of the monomer. In this aspect, the linker unit (B) includes (i) a first portion connected to the trithiocarbonate core unit (A), and (ii) a nitrogen atom connected to the other end of the first portion, and end units (C) comprising two hydrogen atoms connected to the end nitrogen atom of the linker unit. Together, the nitrogen atom and the two hydrogen atoms define an amine. An example of such a trithiocarbonate monomer is illustrated in FIG. 22(A). The first portion of the linking moiety (linker unit), B, may comprise any appropriate group or molecule that is capable of connecting the core unit and forming an amine at its end. The first portion of B may comprise a single alkylene group or a multiple alkylene chain. i.e., $(-CH_2-)_n$ and may be linear or branched. The first portion of B may also comprise one or more carbon-carbon double bonds. In other embodiments, the first portion of B may comprise an aromatic group or multiple aromatic groups. In an embodiment, the first portion of the linker unit B is C1-C10, or C2-C4 alkene i.e., $(-CH_2-)_n$. In an embodiment, the first portion of the linker unit B is C2-C10 or C3-C5 alkenylene. In an embodiment, the first portion of the linker unit B is C2-C10 or C3-C5 alkenylene (comprising at least one carbon-carbon double bond). In other embodiments, the first portion of B may be phenylene or di-phenylene. The first portion of B may also be $(-CH_2-)_n$ where one or more of $(CH_2)$ are replaced with phenylene. In one embodiment, the first portion of B is a C2-C10 alkane (branched or unbranched). In one embodiment, the first portion of B may comprise a branched C2-C10 alkane, where one or more of the $(CH_2)$ branches of the alkane are replaced by various electron-withdrawing groups (EWG's) including, for example, cyano (CN), nitro ($NO_2$), trihalides, carboxylic acids, sulfonates, esters, ketones, and aldehydes. In one embodiment, the first portion of B is a C2-C10 alkene (branched or unbranched, and cis or trans). In one embodiment, the first portion of B is a C2-C10 alkyne. In one embodiment, the first portion of B is an aromatic ring. In one embodiment, the first portion of B may include an C2 or higher alkane, such as the alkane shown in FIG. 15a. In one embodiment, the first portion of B may include a C3 or higher alkene, such as the alkene shown in FIG. 15b. In one embodiment, the first portion of B may include a benzylic group, such as the benzylic group shown in FIG. 15c. In one embodiment, the first portion of B may include a phenyl group, such as the phenyl group shown in FIG. 15d. In one embodiment, the first portion of B may include a diphenyl group, such as the diphenyl group shown in FIG. 15e. Any of the above-described monomers may be polymerized (e.g., with an appropriate mixture, described below) to form a covalently adaptable network.

When producing trithiocarbonate monomers having amines at the ends thereof, methods similar to those shown in Schemes 1 and 2 may be employed. In one embodiment, a method may include reacting carbon disulfide ($CS_2$) in the presence of one of (a) a halogenated carbon-compound, or (b) a salt or ester of a sulfonic acid. The halogenated carbon-compound may be selected from the group consisting of an alkyl halide, a vinyl halide and a benzylic halide. The sulfonic acid may be selected from the group consisting of mesylates, tosylates, nosylates, and brosylates. A nitrogen atom of a carbamate is connected to an end of the halogenated carbon-compound or the salt or ester of the sulfonic acid. The step of reacting carbon disulfide may include completing the reacting in a polar aprotic solvent at a temperature of from 10° to 100° C. Generally, stoichiometric amounts of carbon disulfide are present so as to restrict formation of excess by-products. In one embodiment, the reacting step occurs at a temperature of from 10° to 80° C. In one embodiment, reacting step occurs at a temperature of from 10° to 60° C. In one embodiment, reacting step occurs at a temperature of from 10° to 40° C. In one embodiment, the reacting step occurs at a temperature of at least ambient. The method may further include, forming, due to the reacting, reaction products, wherein the reaction products at least include first products, wherein the first products are a compound comprising a trithiocarbonate core unit (A) and two linker units (B). Each of the two linker units comprises a first portion and a second portion. Each of the two linker units are connected to the core unit via the first portion. The first portion may be selected from the group consisting of an alkane, an alkene, and a benzylic group. The second portion generally comprises the carbamate connected to the first portion via the nitrogen atom of the carbamate.

As used herein, "carbamate" and the like means a chemical compound having the following chemical structure:

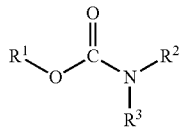

where $R^2$ is generally the first portion of the linker unit to be connected to the core unit, where $R^1$ is generally any suitable stabilizing group or compound, such a tert-butyl group, and where $R^3$ is generally hydrogen.

When producing trithiocarbonate monomers having amines at the ends thereof, the method may include cleaving the carbamate at the nitrogen atom, thereby producing second products having end units (C) connected to each of the linker units, wherein the end units comprise two hydrogen atoms, thereby, in combination with the nitrogen atom of each of the linker units, providing an amine group. In one embodiment, the removing step comprises contacting the first product with a removing agent solution, and the contacting may occur at a temperature of from 248K to 313K (−25° C. to 40° C.). In one embodiment, the contacting occurs at a temperature of from 258K to 303K. In one embodiment, the contacting occurs at a temperature of from 268K to 293K. In one embodiment, the contacting occurs at a temperature of from 270K to 280K. In one embodiment, the removing agent solution is an acid. The acid may be any suitable acid, such as phosphoric acid, trifluoroacetic acid, HCl, among others.

In another aspect, the invention provides allyl sulfide monomers comprising an allyl sulfide core unit (A) with amines at the ends of the monomer. In this aspect, the linker unit (B) includes (i) a first portion connected to the allyl sulfide core unit (A), and (ii) a nitrogen atom connected to the other end of the first portion, and end units (C) comprising two hydrogen atoms connected to the end nitrogen atom of the linker unit. Together, the nitrogen atom and the two hydrogen atoms define an amine. The first portion of the linking moiety (linker unit), B, may comprise any appropriate group or molecule that is capable of connecting the with the core unit and forming an amine at its end. An example of such a allyl sulfide monomer is illustrated in FIG. 22(B). The first portion of B may comprise a single alkylene group or a multiple alkylene chain. i.e., (—$CH_2$—)$_n$ and may be linear or branched. The first portion of B may also comprise one or more carbon-carbon double bonds. In other embodiments, the first portion of B may comprise an aromatic group or multiple aromatic groups. In an embodiment, the first portion of the linker unit B is C1-C10, or C2-C4 alkene i.e., (—$CH_2$—)$_n$. In an embodiment, the first portion of the linker unit B is C2-C10 or C3-C5 alkenylene. In an embodiment, the first portion of the linker unit B is C2-C10 or C3-C5 alkenylene (comprising at least one carbon-carbon double bond). In other embodiments, the first portion of B may be phenylene or di-phenylene. The first portion of B may also be (—$CH_2$—)$_n$ where one or more of ($CH_2$) are replaced with phenylene. In one embodiment, the first portion of B is a C2-C10 alkane (branched or unbranched). In one embodiment, the first portion of B may comprise a branched C2-C10 alkane, where one or more of the ($CH_2$) branches of the alkane are replaced by various electron-withdrawing groups (EWG's) including, but not limited to, cyano (CN), nitro ($NO_2$), trihalides, carboxylic acids, sulfonates, esters, ketones, and aldehydes. In one embodiment, the first portion of B is a C2-C10 alkene (branched or unbranched, and cis or trans). In one embodiment, the first portion of B is a C2-C10 alkyne. In one embodiment, the first portion of B is an aromatic ring. In one embodiment, the first portion of B may include an C2 or higher alkane, such as the alkane shown in FIG. 15a. In one embodiment, the first portion of B may include a C3 or higher alkene, such as the alkene shown in FIG. 15b. In one embodiment, the first portion of B may include a benzylic group, such as the benzylic group shown in FIG. 15c. In one embodiment, the first portion of B may include a phenyl group, such as the phenyl group shown in FIG. 15d. In one embodiment, the first portion of B may include a diphenyl group, such as the diphenyl group shown in FIG. 15e. Any of the above-described monomers may be polymerized (e.g., with an appropriate mixture, described below) to form a covalently adaptable network.

When producing allyl sulfide monomers having amines at the ends thereof, methods similar to those shown in Schemes 3 and 4 may be employed. For instance, the allyl sulfide monomers may be synthesized by formation of a core allyl disulfide scaffold with amine groups at both ends. The core allyl disulfide scaffold may be formed by reaction of two equivalents of a thio-amine or thio-Boc(amine) with one equivalent of 3-chloro-2-chloromethyl-1 propene in a solution of sodium methoxide or suitable base able to deprotonate the sulfur. If the amine is used, no further synthetic steps are required. If the Boc-protected amine is used, an acidic deprotection step may be used to liberate the free amine.

In another aspect, the invention provides trithiocarbonate monomers comprising a trithiocarbonate core unit (A) and alkynes as the end units (C). The first portion of the linking moiety (linker unit), B, may comprise any appropriate group capable of connecting the core unit to the alkyne. An example of such a trithiocarbonate monomer is illustrated in FIG. 23(A). In one embodiment, B may comprise a single alkylene group or a multiple alkylene chain. i.e., (—$CH_2$—)$_n$ and may be linear or branched. B may also comprise one or more carbon-carbon double bonds. In other embodiments, B may comprise an aromatic group or multiple aromatic groups. In an embodiment, the linker unit B is C1-C10, or C2-C4 alkene i.e., (—$CH_2$—)$_n$. In an embodiment, the linker unit B is C2-C10 or C3-C5 alkenylene. In an embodiment, the linker unit B is C2-C10 or C3-C5 alkenylene (comprising at least one carbon-carbon double bond). In other embodiments, B may be phenylene or di-phenylene. B may also be (—$CH_2$—)$_n$ where one or more of ($CH_2$) are replaced with phenylene. In one embodiment, B is a C2-C10 alkane (branched or unbranched). In one embodiment, B may comprise a branched C2-C10 alkane, where one or more of the ($CH_2$) branches of the alkane are replaced by various electron-withdrawing groups (EWG's) including, for example, cyano (CN), nitro ($NO_2$), trihalides, carboxylic acids, sulfonates, esters, ketones, and aldehydes. In one embodiment, B is a C2-C10 alkene (branched or unbranched, and cis or trans). In one embodiment, B is a C2-C10 alkyne. In one embodiment, B is an aromatic ring. In one embodiment, B may include an C2 or higher alkane, such as the alkane shown in FIG. 15a. In one embodiment, B may include a C3 or higher alkene, such as the alkene shown in FIG. 15b. In one embodiment, B may include a benzylic group, such as the benzylic group shown in FIG. 15c. In one embodiment, B may include a phenyl group, such as the phenyl group shown in FIG. 15d. In one embodiment, B may include a diphenyl group, such as the diphenyl group shown in FIG. 15e. Any of the above-described monomers may be polymerized (e.g., with an appropriate mixture, described below) to form a covalently adaptable network.

When producing trithiocarbonate monomers having alkyne end units, methods similar to those shown in Scheme 1 may be used. Scheme 2 may not be required as the alkyne end unit may be present during the reacting step. In one embodiment, a method may include reacting carbon disulfide ($CS_2$) in the presence of one of (a) a halogenated carbon-compound, or (b) a salt or ester of a sulfonic acid. The halogenated carbon-compound may be selected from the group consisting of an alkyl halide, a vinyl halide and a benzylic halide. The sulfonic acid may be selected from the group consisting of mesylates, tosylates, nosylates, and brosylates. An alkyne is connected to an end of the halogenated carbon-compound or the salt or ester of the sulfonic acid. The method may include forming, due to the reacting, reaction products, wherein the reaction products at least include first products, wherein the first products are a compound comprising a trithiocarbonate core unit (A), two linker units (B), and two end units (C). The two linker units (B) are selected from the group consisting of an alkane, an alkene, and a benzylic group, and the end units (C) are alkynes.

In another aspect, the invention provides allyl sulfide monomers comprising an allyl sulfide core unit (A) and alkynes as the end units (C). The first portion of the linking moiety (linker unit), B, may comprise any appropriate group capable of connecting the core unit to the alkyne. An example of such an allyl sulfide monomer is illustrated in FIG. 23(B). In one embodiment, B may comprise a single alkylene group or a multiple alkylene chain. i.e., $(-CH_2-)_n$ and may be linear or branched. B may also comprise one or more carbon-carbon double bonds. In other embodiments, B may comprise an aromatic group or multiple aromatic groups. In an embodiment, the linker unit B is C1-C10, or C2-C4 alkene i.e., $(-CH_2-)_n$. In an embodiment, the linker unit B is C2-C10 or C3-C5 alkenylene. In an embodiment, the linker unit B is C2-C10 or C3-C5 alkenylene (comprising at least one carbon-carbon double bond). In other embodiments, B may be phenylene or di-phenylene. B may also be $(-CH_2-)_n$ where one or more of ($CH_2$) are replaced with phenylene. In one embodiment, B is a C2-C10 alkane (branched or unbranched). In one embodiment, B may comprise a branched C2-C10 alkane, where one or more of the ($CH_2$) branches of the alkane are replaced by various electron-withdrawing groups (EWG's) including, for example, cyano (CN), nitro ($NO_2$), trihalides, carboxylic acids, sulfonates, esters, ketones, and aldehydes. In one embodiment, B is a C2-C10 alkene (branched or unbranched, and cis or trans). In one embodiment, B is a C2-C10 alkyne. In one embodiment, B is an aromatic ring. In one embodiment, B may include an C2 or higher alkane, such as the alkane shown in FIG. 15a. In one embodiment, B may include a C3 or higher alkene, such as the alkene shown in FIG. 15b. In one embodiment, B may include a benzylic group, such as the benzylic group shown in FIG. 15c. In one embodiment, B may include a phenyl group, such as the phenyl group shown in FIG. 15d. In one embodiment, B may include a diphenyl group, such as the diphenyl group shown in FIG. 15e. Any of the above-described monomers may be polymerized (e.g., with an appropriate mixture, described below) to form a covalently adaptable network.

When producing allyl sulfide monomers having alkynes at the ends thereof, methods similar to those shown in Scheme 3 may be employed. Scheme 4 may not be required as the alkyne end unit may be present during the reacting step. For instance, the allyl sulfide monomers may be synthesized by formation of a core allyl disulfide scaffold with alkyne groups at both ends. The core allyl disulfide scaffold may be formed by reaction of two equivalents of a thio-alkyne with one equivalent of 3-chloro-2-chloromethyl-1 propene in a solution of sodium methoxide or suitable base able to deprotonate the sulfur.

Two main classes of synthons used in CANs that contain RAFT moieties are the allyl sulfides and the trithiocarbonates (TTC). FIG. 3 schematically illustrates AFT monomer in a network (large dots are AFT groups). By taking advantage of the reactivity of RAFT synthons polymerized with a functional group, a polymer network can be formed by a photo-catalyzed radical thiol-ene reaction (FIG. 4a) or by a base (or nucleophile) catalyzed thiol-ene Michael addition reaction (FIG. 4b).

When the network is formed by a photocatalyzed radical polymerization, AFT reactions occur concurrently with and subsequent to polymerization. In contrast, when the thiol-Michael addition reaction is used, the AFT mechanism occurs only during post-polymerization rearrangement of the network. Uniquely, the differences in when the AFT rearrangement of the network occurs relative to polymerization, as well as differences in the resulting network structure, optical characteristics of the material, and other physical properties of the material are readily adjusted simply by changing the polymerization mechanism.

In another aspect, the invention provides covalently adaptable networks incorporating the CRAFT monomers of the invention as well as kits and methods for synthesizing these networks. In an embodiment, a CAN may constructed using a base catalyzed thiol-Michael "click" reaction by reacting stoichiometric mixtures (1:1 (meth)acrylate:thiol functional group ratio) of a (meth)acrylate trithiocarbonate or allyl sulfide component and a thiol monomer component. The (meth)acrylate component comprises at least one (meth)acrylate monomer while the thiol monomer component comprises at least one thio monomer. In an embodiment, the thiol monomer component may comprise pentaerytheritol tetrakis (3-mercaptopropionate) (PETMP) or another polythiol monomer. In an embodiment, the (meth)acrylate component may comprise the RAFT trithiocarbonate or allyl sulfide monomer and a (meth)acrylate monomer other than a RAFT monomer. In an embodiment, the (meth)acrylate monomer other than a RAFT monomer may comprise tetraethylene glycol diacrylate (TEGDA) or another diacrylate monomer. In an embodiment, the RAFT monomer comprises from 25-40% by weight of the mixture including the meth(acrylate component) and the thiol component. In an embodiment, the RAFT monomer comprises from 30-35% by weight of the mixture including the meth(acrylate component) and the thiol component. In an embodiment, the RAFT monomer comprises from 32-34% by weight of the mixture including the meth(acrylate component) and the thiol component.

In another embodiment, a CAN may be synthesized through chain growth polymerization. In an embodiment, a CAN may be synthesized through chain growth polymerization of a mixture comprising a (meth)acrylate trithiocarbonate or allyl sulfide monomer of the invention and a polymerization initiator. In an embodiment, the mixture further comprises a (meth)acrylate monomer which does not include a RAFT functionality. In one embodiment, the molar ratio of RAFT functionalities to (meth)acrylate functionalities is 0.0025 to 0.1 (i.e. 0.25% to 10%). In another embodiment, the molar ratio of RAFT functionalities to (meth)acrylate functionalities is 0.0025 to 0.05 (i.e. 0.25% to 5%). In yet another embodiment, the molar ratio of RAFT functionalities to (meth)acrylate functionalities is 0.005 to 0.05 (i.e. 0.5% to 5%). In another embodiment, the molar ratio of RAFT functionalities to (meth)acrylate functionalities is 0.005 to 0.025 (i.e. 0.5% to 2.5%). In yet another embodiment, the molar ratio of RAFT functionalities to (meth)acrylate functionalities is 0.01 to 0.15 (1% to 15%). In another embodiment, the molar ratio of RAFT functionalities to (meth)acrylate functionalities is 0.02 to 0.15 (2% to 15%). In yet another embodiment, the molar ratio of RAFT functionalities to (meth)acrylate functionalities is 0.05 to 0.15 (5% to 15%). In another embodiment, the molar ratio of RAFT functionalities to (meth)acrylate functionalities is 0.075 to 0.15 (7.5% to 15%). In yet another embodiment, the molar ratio of RAFT functionalities to (meth)acrylate functionalities is 0.1 to 0.15 (10% to 15%). The molar ratio of the first monomer to initiator may be from 0.05 to 10%. The molar ratio of the first monomer to initiator may be 1% to 5%. In some embodiments, the wt % of the RAFT monomer in the mixture may be from 1 wt % to 15 wt %. In one embodiment, the wt % of the RAFT monomer in the mixture may be from 1 wt % to 10 wt %. In another embodiment, the wt % of the RAFT monomer in the mixture may be from 1 wt % to 3 wt %. In yet another embodiment, the wt % of the RAFT monomer in the mixture may be from 2 wt % to 5 wt %. In another embodiment, the wt % of the RAFT monomer in the mixture may be from 5 wt % to 15 wt %. In yet another embodiment, the wt % of the RAFT monomer in the mixture may be from 5 wt % to 10 wt %. In some embodiments, the wt % RAFT monomer may be (a) about 10% for alkyl TTC monomer or an allyl sulfide monomer, (b) about 1.5% for an alkene TTC monomer, or (c) about 2.5 wt % for a benzyl TTC monomer (in an embodiment, the variation in the wt % is +/−20% or +/−10%). The amount of RAFT monomer in the mixture may be selected to obtain a desired degree of acrylate conversion.

In another embodiment, a CAN of the invention may be synthesized through a mixed-mode polymerization. In an embodiment, a CAN may be synthesized through polymerization of a mixture comprising a (meth)acrylate trithiocarbonate or allyl sulfide monomer of the invention, a thiol monomer and a polymerization initiator. In an embodiment, the mixture further comprises a (meth)acrylate monomer which does not include a RAFT functionality.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. When a Markush group or other grouping is used herein, all individual members of the group and all combinations and subcombinations possible of the group are intended to be individually included in the disclosure.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions that have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The following definitions are provided to clarify their specific use in the context of the invention.

Although the description herein contains many specificities, these should not be construed as limiting the scope of the invention but as merely providing illustrations of some of the presently preferred embodiments of the invention. For example, thus the scope of the invention should be determined by the appended claims and their equivalents, rather than by the examples given.

DETAILED DESCRIPTION

The invention may be further understood by the following non-limiting examples.

EXAMPLE 1

Synthesis of Monomers

In this paper, a mild and efficient synthesis of (meth)acrylate functionalized trithiocarbonates and allyl sulfides exhibiting controlled reversible addition-fragmentation termination (CRAFT) monomers is described, and their efficiency in photoinduced stress relaxation during and post polymerization is demonstrated.

The synthons consisted of an AFT core (A) that was either an allyl sulfide or trithiocarbonate moiety. The linker (B) was synthetically connected to the AFT core (A) and capped with an end group (C). The linkers included into the AFT monomers were chosen to elicit specific mechanical behavior from the final networks and also to induce various electronic effects on the AFT process. Tailored at the ends of the AFT monomers are (C) segments that consist generally of a polymerizable subunit, here, specifically an acrylate. The A, B, and C subunits that were systematically evaluated are presented in (Table 1).

TABLE 1

Monomers

A: Example Invention Trithiocarbonates

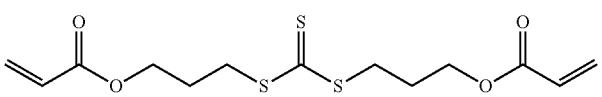 [SMILES: C=CC(=O)OCCCSC(=S)SCCCOC(=O)C=C]

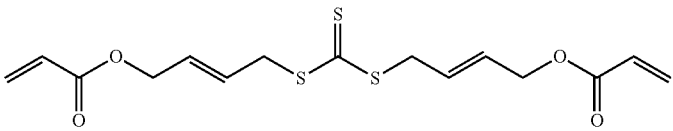 [SMILES: C=CC(=O)OC/C=C/CSC(=S)SC/C=C/COC(=O)C=C]

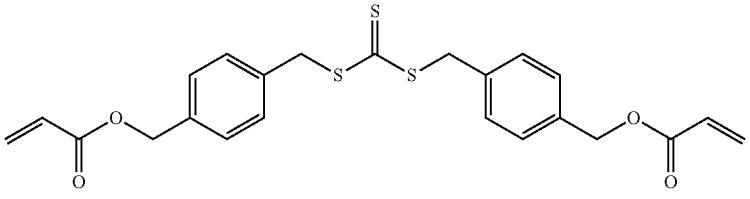 [SMILES: C=CC(=O)OCc1ccc(CSC(=S)SCc2ccc(COC(=O)C=C)cc2)cc1]

B: Example Invention Allyl Sulfides

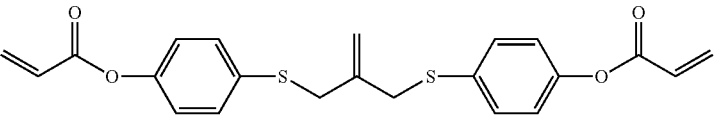 [SMILES: C=CC(=O)Oc1ccc(SCC(=C)CSc2ccc(OC(=O)C=C)cc2)cc1]

TABLE 1-continued

Monomers

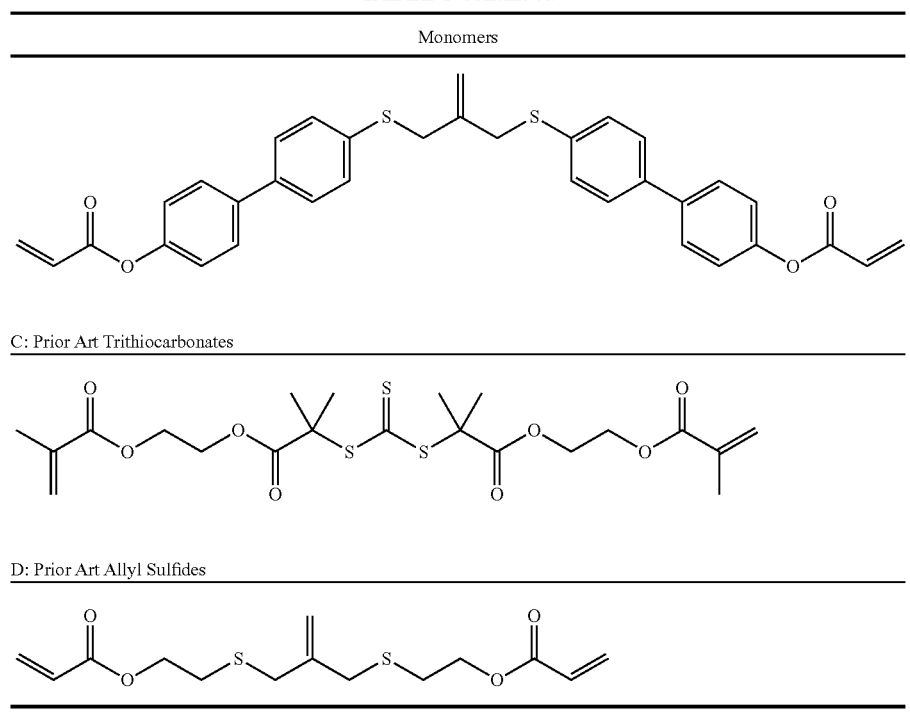

C: Prior Art Trithiocarbonates

D: Prior Art Allyl Sulfides

Figure 17:
FIG. 17 illustrates an example synthesis method for producing monomers using a trithiocarbonate anion.

The key reaction to build the trithiocarbonate backbone used the reaction of carbon disulfide with a mild base, potassium carbonate, in a polar aprotic solvent with an alkyl halide, vinyl halide or benzylic halide, which contained a silyl protected alcohol at one end (FIG. 17, Scheme 1).

Figure 18:
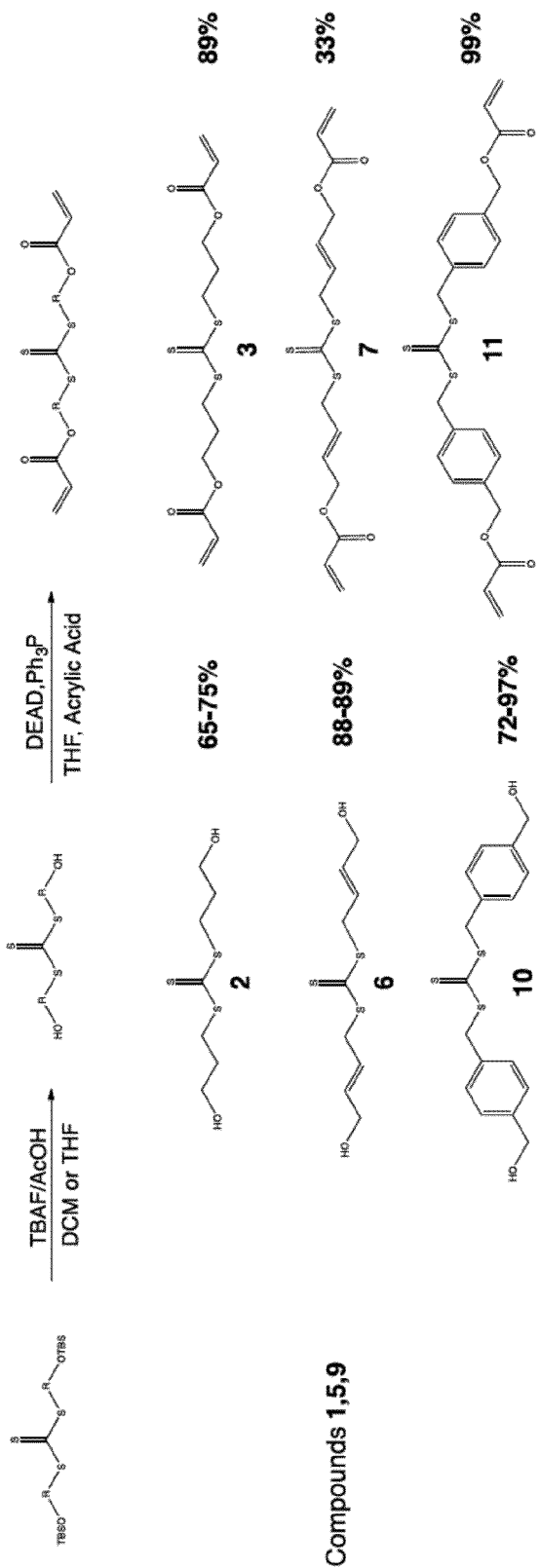
FIG. 18 illustrates an example synthesis method for producing diacrylate functionalized RAFT agents.

The alcohol was subsequently deprotected using TBAF/AcOH, which allows the use of fluorine to deprotect the silyl group without allylation of the AFT core by TBAF. The deprotection is followed by a Mitsunobu coupling to add the (meth)acrylate end groups (FIG. 18, Scheme 2). Because of its unique self-healing properties, and the monomer is a methacrylate capped symmetrical molecule, S,S'-bis(isobutyric acid)-trithiocarbonate was synthesized to evaluate its properties against the newly formed trithiocarbonates.

Figure 19:
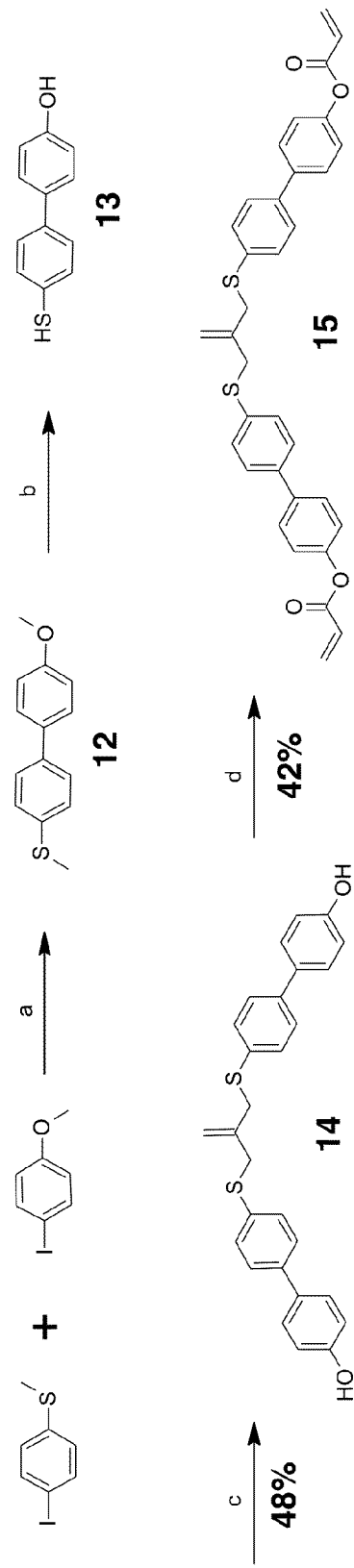
FIG. 19 illustrates one manner of synthesizing a biphenyl allyl sulfide diacrylate.

The allyl sulfides were synthesized as follows. To 3-chloro-2-chloromethyl-1-propene was added the thio-alcohol in a solution of sodium methoxide. The thio-alcohols used were mercaptoethanol, thiophenol, and 4-hydroxyl-4'-mercaptobiphenyl. 4-Hydroxyl-4'-mercaptobiphenyl was synthesized from 4-iodoanisol and 4-bromothioanisol via a Kumada coupling. The product was subsequently reduced with sodium ethanethiolate to yield the 4-hydroxyl-4'-mercaptobiphenyl (FIG. 19, Scheme 3).

Figure 20:
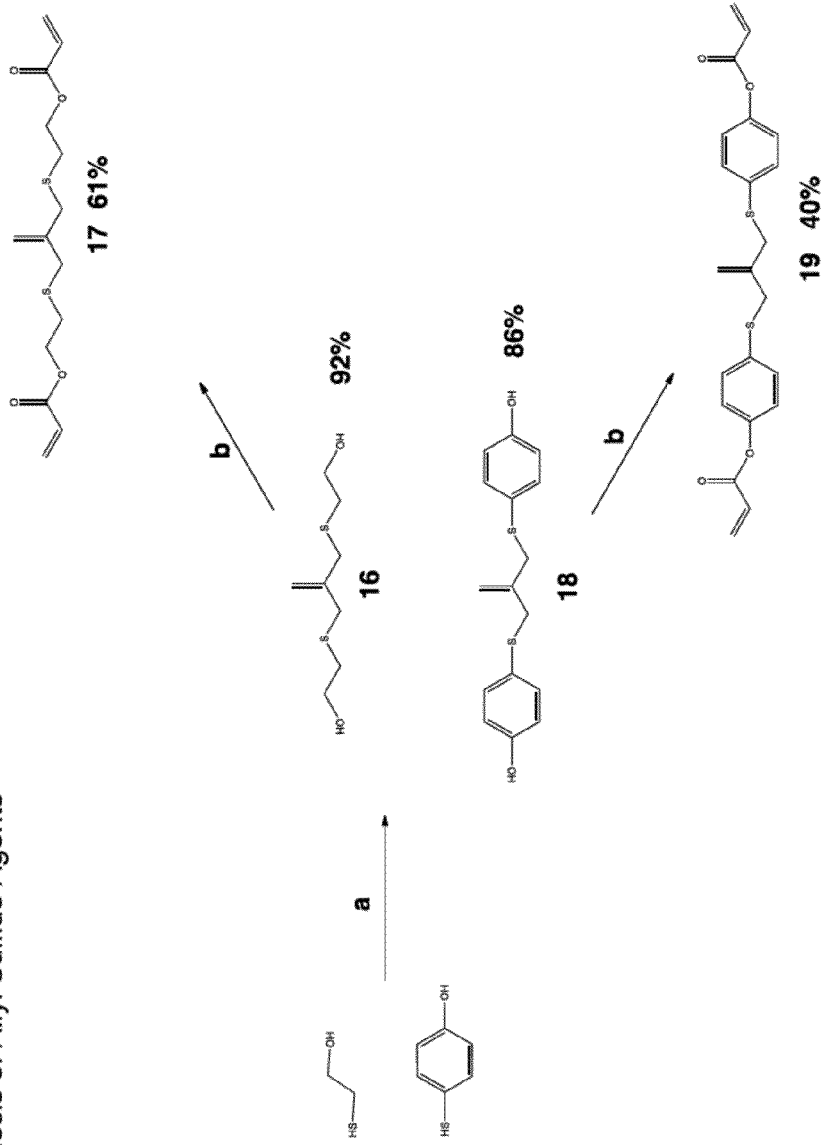
FIG. 20 illustrates one synthesis method for producing allyl sulfide agents.

Once all the thio-alcohols were in hand, the core allyl disulfide scaffold was formed. The acrylate or methacrylate was added to the pendent alcohol using modified Schotten-Baumann conditions, where the acyl chloride is reacted with the alcohol using triethylamine as an acid scavenger. (FIG. 20, Scheme 4). The acid chloride reaction to produce the diester acrylate functionality was used because the ease of the reaction conditions and the cost of acryloyl chloride. The reaction can be done using Mitsunobu conditions, as well. The Mitsunobu reaction gives overall better yields, but the purification of the final product is difficult since the DEAD and triphenylphosphine bi-products are hard to separate from the final product.

EXAMPLE 2

Figure 4A:
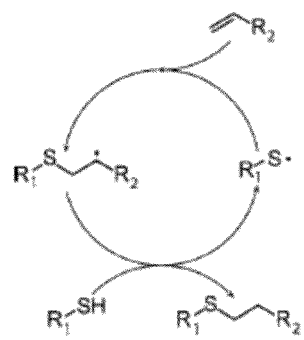
FIG. 4 illustrates both (a) a Thiol-ene radical reaction, and (b) a Thiol-ene Michael addition reaction.
Figure 4B:
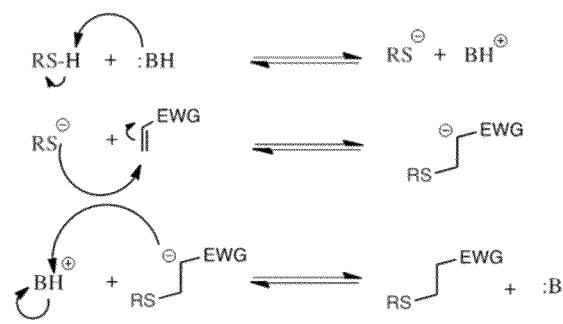

Incorporation of Monomers into Polymer Networks by Thiol-Michael Addition Reaction The monomers were incorporated into polymer networks to evaluate each monomer's individual effects on the polymer network. For the acrylate functionalized AFT synthons, a polymer network can be formed either by a photocatalyzed radical polymerization or by a base (or nucleophile) catalyzed thiol-Michael addition reaction (FIG. 4a, 4b).

Figure 5:
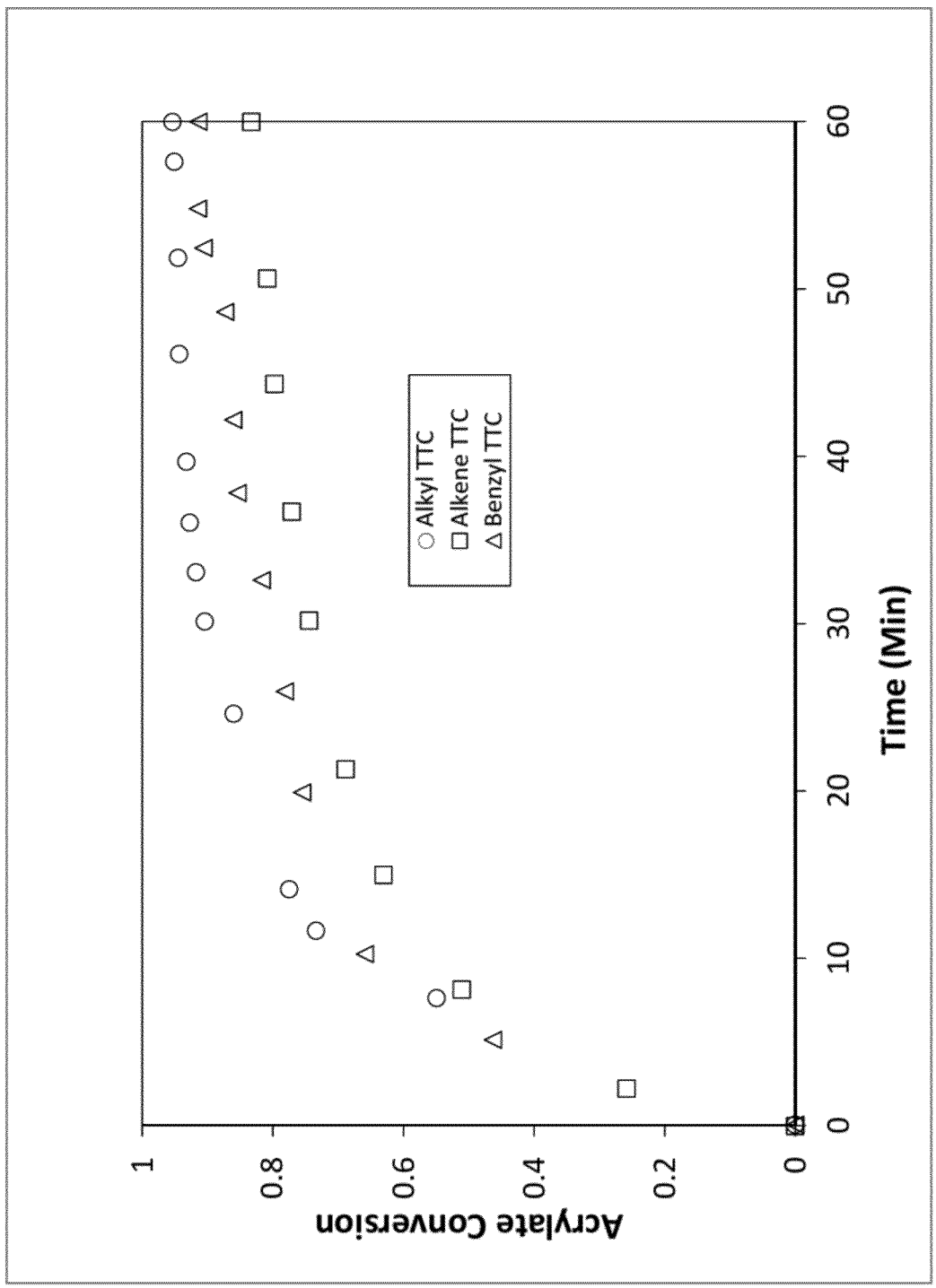
FIG. 5 is a graph illustrating IR kinetics of trithiocarbonate conversion relative to Example 2. The acrylate conversion of the nonfunctional diacrylate control composed of 70% Bisphenol A ethoxylated diacrylate and 30% tetraethylene glycol diacrylate as a function of time, as well as when a portion of the TEGDA is replaced with the trithiocarbonate diacrylates as follows: 10% alkyl, 1.5% alkene, and 2.0% benzyl. The samples were irradiated at 5 mW/cm$^2$ with 365 nm light for 10 minutes.

The trithiocarbonate networks were constructed using a base catalyzed thiol-Michael "click" reaction by reacting stoichiometric mixtures (1:1 acrylate:thiol functional group ratio) of pentaerytheritol tetrakis (3-mercaptopropionate) (PETMP) and tetraethylene glycol diacrylate (TEGDA) and the RAFT trithiocarbonate. The CRAFT monomer containing networks conversion and kinetics were evaluated for 60 minutes by IR spectroscopy after the addition of 1% triethylamine as the thiol-Michael catalyst (FIG. 5).

Figure 6:
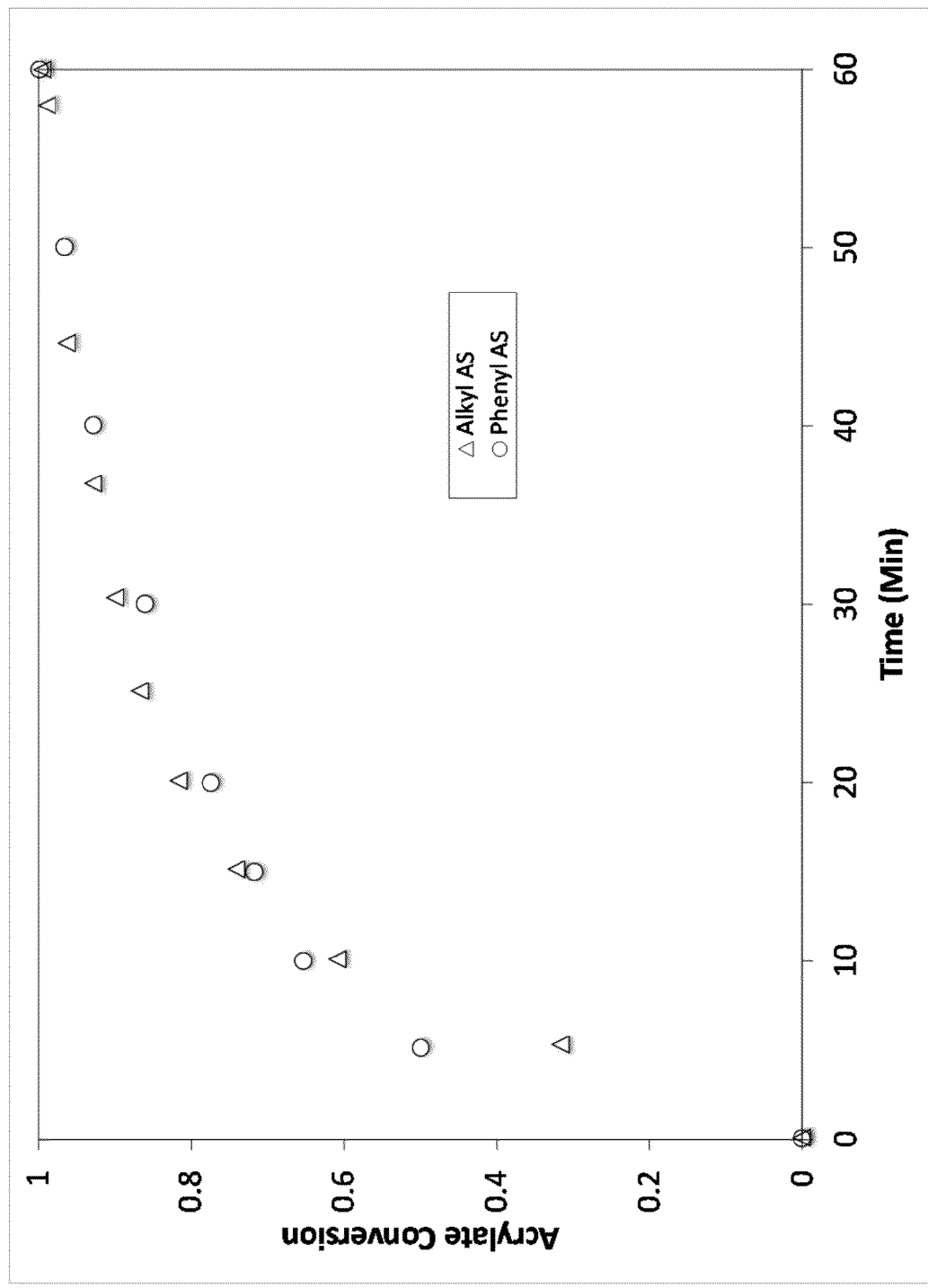
FIG. 6 is a graph illustrating IR kinetics of ally sulfide conversion relative to Example 2. The acrylate conversion of the nonfunctional diacrylate control composed of 70% Bisphenol A ethoxylated diacrylate and 30% tetraethylene glycol diacrylate as a function of time as well as diluted with the allyl sulphides as follows: 10% alkyl and 10% phenyl. The samples were irradiated at 5 mW/cm$^2$ at 365 nm for 10 minutes using 0.25% DMPA

The allyl sulfide networks were constructed using the same base catalyzed thiol-Michael "click" reaction by reacting stoichiometric mixtures (1:1 acrylate:thiol functional group ratio) of pentaerytheritol tetrakis (3-mercaptopropionate) (PETMP) and tetraethylene glycol diacrylate (TEGDA) and the allyl sulfide The CRAFT monomer containing networks conversion and kinetics were evaluated for 60 minutes by IR spectroscopy after the addition of 1% triethylamine or 0.8% imidazole as the thiol-Michael catalyst, respectively (FIG. 6).

The previously made thio-Michael networks were evaluated on a dynamic mechanical analyzer (DMA) to analyze the how the different monomers affected the glass transition and elastic moduli of the networks (Table 2).

TABLE 2

Glass transition temperature and elastic modulus (E)

| RAFT monomer used in the resin formulation (Thiol/Acrylate ratio) | $T_g$ (°C.) | Rubbery E' at 40° C. (MPa) |
|---|---|---|
| Alkyl trithiocarbonate | −9.7 ± 0.2 | 10 ± 1 |
| S,S'-bis(isobutyric acid)-trithiocarbonate | −13.6 ± 0.6 | 2 ± 2 |
| Alkene trithiocarbonate | −3.1 ± 0.5 | 19.8 ± 0.1 |
| Benzyl Trithiocarbonate | 9.0 ± 0.6 | 18.0 ± 0.3 |
| Alkyl Allyl Sulfide | −8 ± 1 | 24 ± 5 |
| Phenyl Allyl Sulfide | 13.3 ± 0.8 | 15 ± 2 |
| Bi-Phenyl Allyl Sulfide | 29.8 ± 0.7 | 24 ± 2 |

In the thiol-Michael catalyzed networks, the trithiocarbonates showed a reduced rate of conversion as the monomers became bulkier and more rigid. On the other hand, the phenyl allyl sulfide network was made with 0.8% imidazole, where the allyl alkyl sulfide network was formed from 1% triethylamine. The $pK_a$ of imidazole is 7.0 compared to that of triethylamine, which is 11.0. Even with a base that is 10,000 times less basic, the rate of conversion of the phenyl substituent was only slightly slower that than the alkyl allyl sulfide with triethylamine. This phenomenon can be accounted for by the stabilization of the thiol-Michael anion intermediate by the resonance of the phenyl ring.

The rubbery moduli of the networks showed little difference between the CRAFT monomers used in the network. The only significant difference in modulus was seen in the S,S'-bis(isobutyric acid)-trithiocarbonate network. Due to the step-growth thiol-Michael network formation, the resins made from these networks traditionally have Tg's below 0° C. With the incorporation of the pi groups, especially the phenyl ring systems, the pi-pi stacking greatly increases the Tg's of the networks containing these molecular interactions.

Stress relaxation properties were evaluated for the CRAFT monomers by incorporating them into an elastomeric network containing 1% photoinitiator (DMPA). The networks were constructed using a base catalyzed thiol-Michael "click" reaction by reacting stoichiometric mixtures of multifunctional thiols and acrylate-based CRAFT monomers. Utilizing this non-photo, non-radical mediated polymerization mechanism, the photointiator is unconsumed during the polymerization and is present to induce post-polymerization photo-induced stress relaxation without degrading or changing the crosslink density of the networks. The CRAFT monomer containing networks were evaluated on a DMA by inducing a strain of 10%, irradiating at 20 mW/cm², and evaluating the evolution of stress relaxation in the network. The CRAFT monomers exhibited stress relaxation results that varied from 9%-73% under these conditions (Table 3)

TABLE 3

| RAFT monomer | Relaxation Time (min) | Relaxation (%) |
|---|---|---|
| Alkyl trithiocarbonate | 3.1 | 12% |
| S,S'-bis(isobutyric acid)-trithiocarbonate (Mat TTC) | 13 | 30% |
| Alkene trithiocarbonate | 1.2 | 45% |
| Benzyl Trithiocarbonate | 2.2 | 54% |
| Alkyl Allyl Sulfide | 2.3 | 52% |
| Phenyl Allyl Sulfide | 1.2 | 75% |
| Bi-Phenyl Allyl Sulfide | 10 | 19% |

Figures 1, 2:
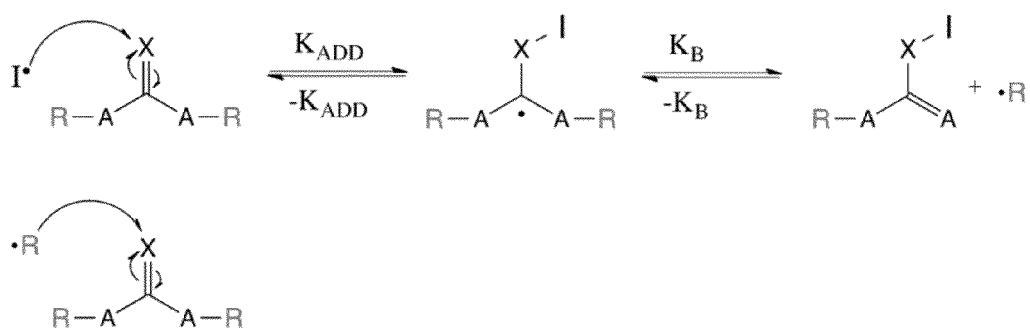
FIG. 1 illustrates an example of a RAFT mechanism.
FIG. 2 illustrates the general structure of the inventive monomers described herein.
Figure 3:
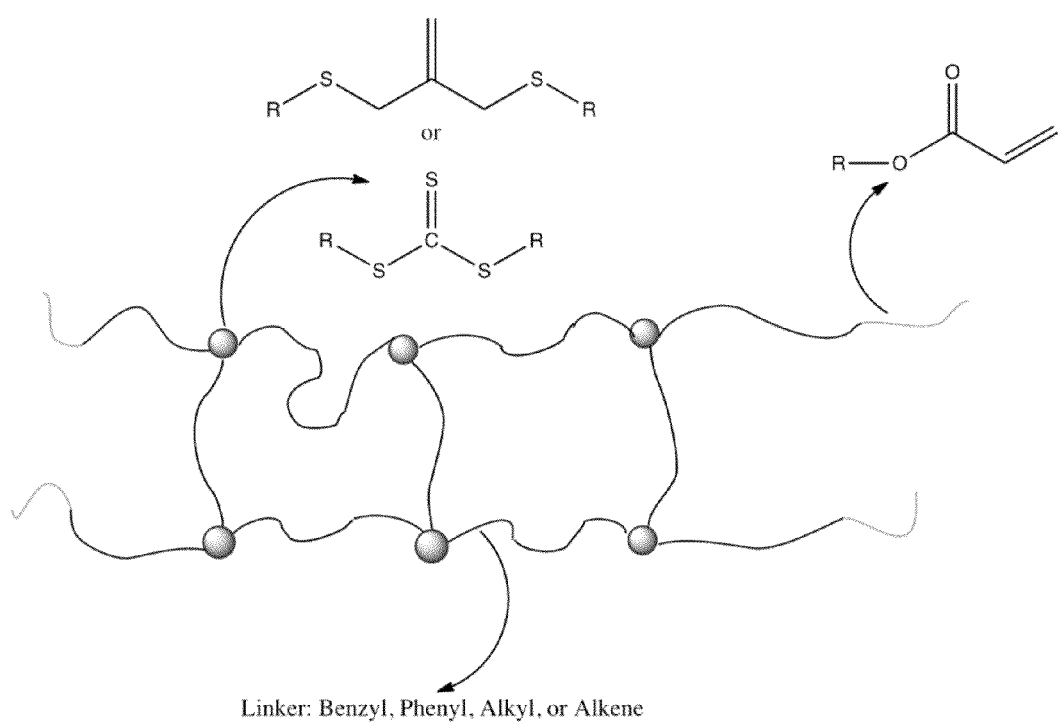
FIG. 3 illustrates a general AFT monomer structure in network.
Figure 7:
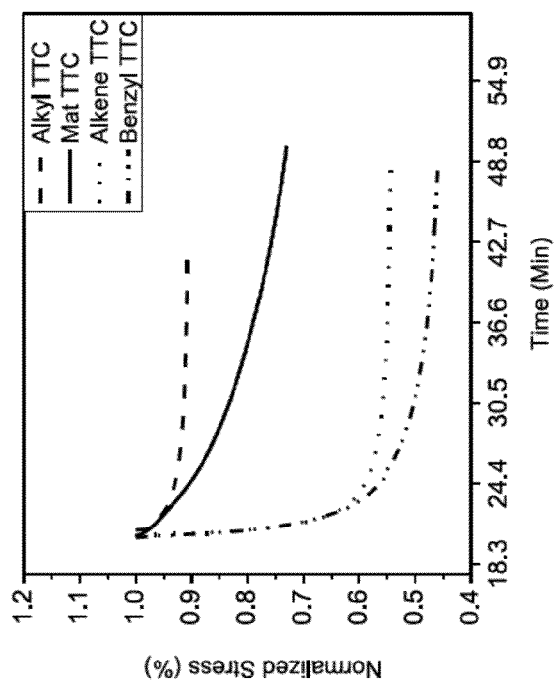
FIG. 7 is a graph illustrating photoresponsive formulation and stress relaxation properties relative to Example 2. Photoresponsive formulation and stress relaxation properties for trithiocarbonate-based networks. The resins were formulated with a 1:1 stoichiometric ratio based on functional groups of PETMP and TEGDA and the RAFT trithiocarbonate at 33 mol percent based on functional groups comprising 50% of the acrylate functionalities as follows: alkyl trithiocarbonate (dash), S,S'-bis(isobutyric acid)-trithiocarbonate (solid), alkene trithiocarbonate (dotted), and benzyl trithiocarbonate (dot-dashed). The RAFT component incorporates trithiocarbonate functional groups into the network strands. Photoinduced stress relaxation (normalized) was performed at 20 mW/cm$^2$ irradiation using 1% by weight DMPA at 365 nm for 30 minutes.
Figure 7:
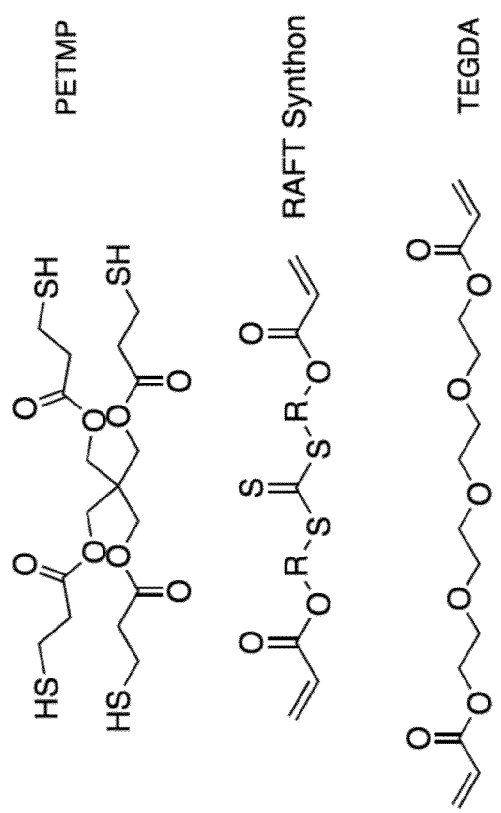
Figure 21:
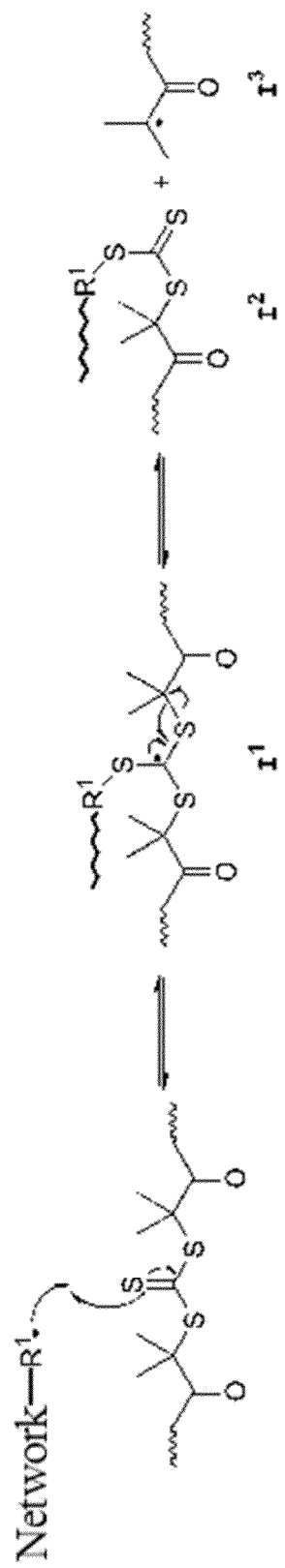
FIG. 21 illustrates a RAFT mechanism within a polymer network, with a radical-mediated AFT bond-exchange mechanism with a trithiocarbonate moiety internal to the polymer network. Going from left to right, a radical generated initially by light exposure adds across the trithiocarbonate within the crosslinked network structure to form a ternary radical. The ternary radical, $I^1$, then rearranges and fragments, either reforming the original structures or replacing the original crosslink with a new crosslink, $I^2$. Leaving group $I^3$ facilitates the continuation of the RAFT process.
Figure 22A:
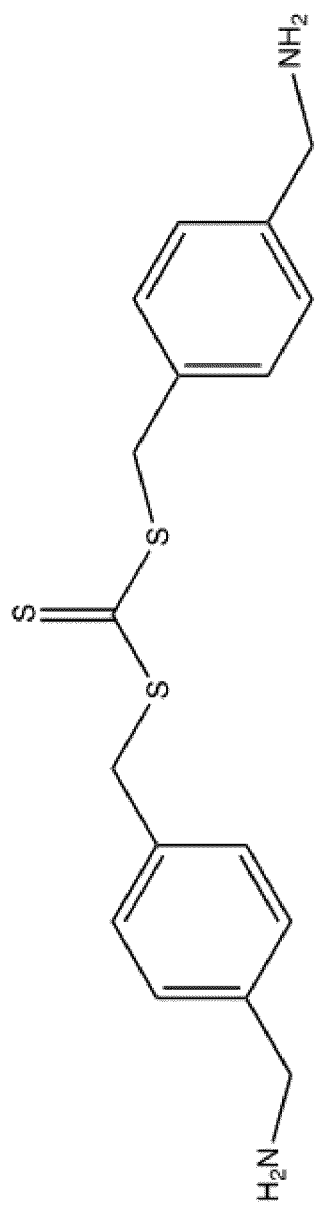
FIGS. 22(A) and (B) illustrate example trithiocarbonate and allyl sulfide monomers, respectively, having amine ends.
Figure 22B:
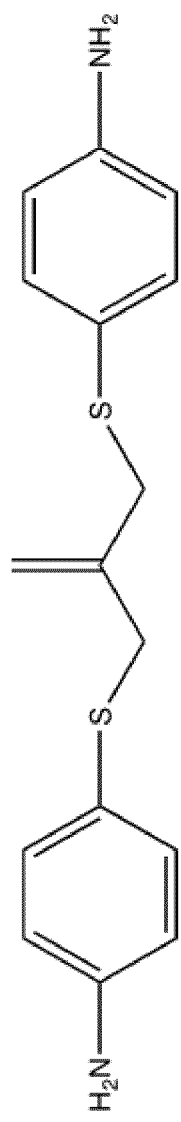
Figure 23A:
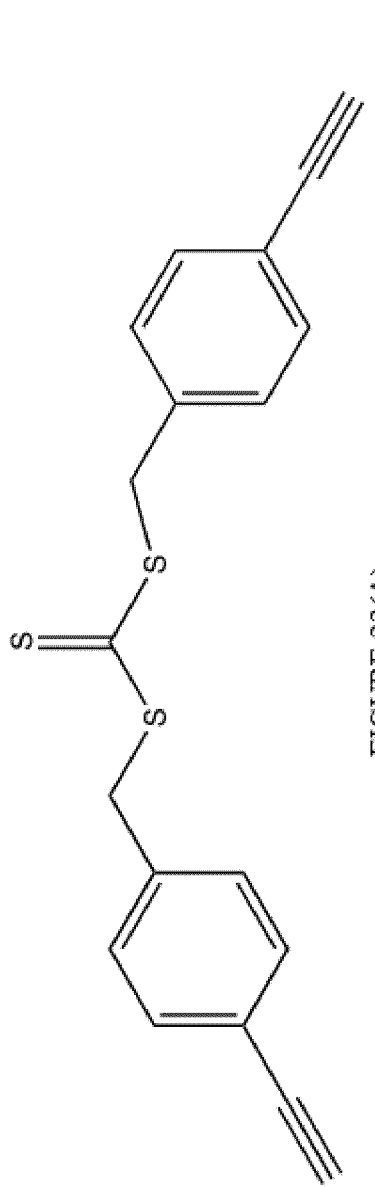
FIGS. 23(A) and (B) illustrate example trithiocarbonate and allyl sulfide monomers, respectively, having alkyne ends.
Figure 23B:
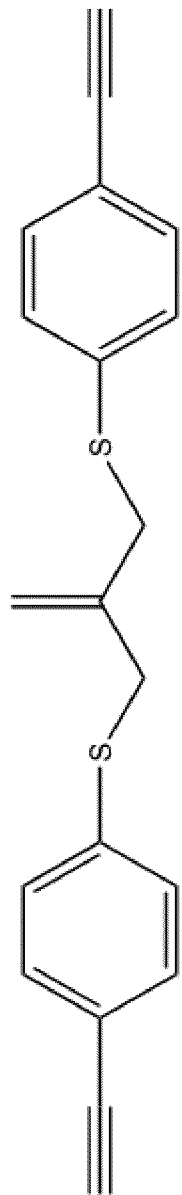

The trithiocarbonates, upon irradiation, showed remarkable stress relaxation in a controlled manner. We hypothesize that these stress relaxation results are indicative of the cleavage rate due to the leaving radical stability $I^3$, as seen in FIGS. 1 and 21, and the relative rate with which $I^3$ will attack another CRAFT center ($C_m$). The new CRAFT monomers were evaluated for their stress relaxation ability relative to a control monomer/polymer, S,S'-bis(R,R'-dimethyl-R"-acetic acid)-trithiocarbonate dimethacrylate, which was synthesized using a procedure from literature[10,22] (FIG. 7) and relative to networks that did not contain any CRAFT monomers. In post stress relaxation studies, we hypothesize that the stability of the leaving carbon radical $I^3$ in the trithiocarbonate systems dominates their ability to relax stress due to the stability of the trithiocarbonate radical intermediate, which can be evaluated.

Figure 8:
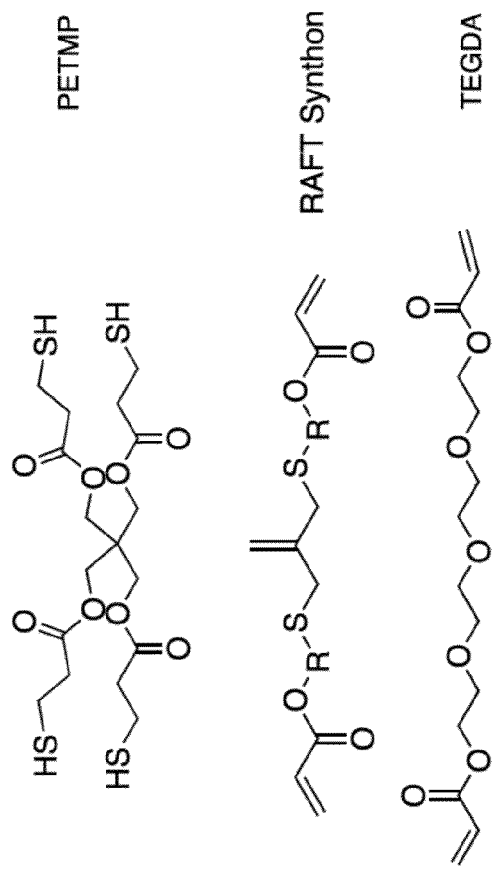
FIG. 8 is a graph illustrating photoresponsive formulation and stress relaxation properties relative to Example 2. Photoresponsive formulation and stress relaxation properties for allyl sulfide-based networks. The resins were formulated with a 1:1 stoichiometric ratio based on functional groups of PETMP and TEGDA and the RAFT allyl sulfide at 33 mol % of the functional groups comprising 50% of the acrylate functionalities as follows: alkyl allyl sulphide (solid), phenyl allyl sulphide (dot), diphenyl allyl sulphide (dash). Photoinduced stress relaxation (normalized) was performed at 20 mW/cm$^2$ irradiation using 1% by weight DMPA at 365 nm for 30 minutes.
Figure 8:
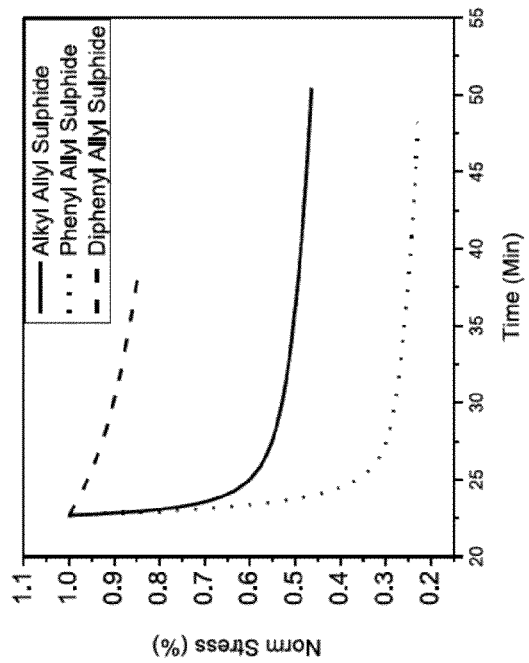

The stress relaxation data suggests this effect is not as prevalent in the allyl sulfide systems, where the radical intermediate is not as stable as its trithiocarbonate counterpart, and the leaving radical is a more stable sulfur radical, not a carbon radical. For post stress relaxation, we believe these factors are what allow the same allyl sulfide radical generated to alleviate more stress in comparison to its trithiocarbonate counterpart (FIG. 8). However, in the allyl sulfide biphenyl system, it is hypothesized that over-enhanced radical stability in the leaving group, $I^3$, generates a radical that attacks neighboring centers, $C_m$, so slowly that little relaxation in the network is seen. With the understanding of these two competing mechanisms, CRAFT agents can be designed to rapidly alleviate the stress in a system. It is also noteworthy to mention the incorporation of different functional groups into the CRAFT monomers, and how these modifications affect network properties. The incorporation of alkene, phenyl, and biphenyl linkers within the system have not only radical stabilizing merit, but these functional groups permit pi interactions within the network that effect the $T_g$ and elastic modulus (E') of these networks (Table 2).

EXAMPLE 3

Incorporation of Monomers into Polymer Networks by Chain Growth

CRAFT monomers were formulated into a chain-growth polymerization network. The monomers were evaluated on their ability to affect the polymerization rate and conversion of an acrylate polymerization system, as RAFT monomers. The monomers incorporated were specifically designed to affect the RAFT mechanism and thereby their ability to control the polymerization.

Figure 9:
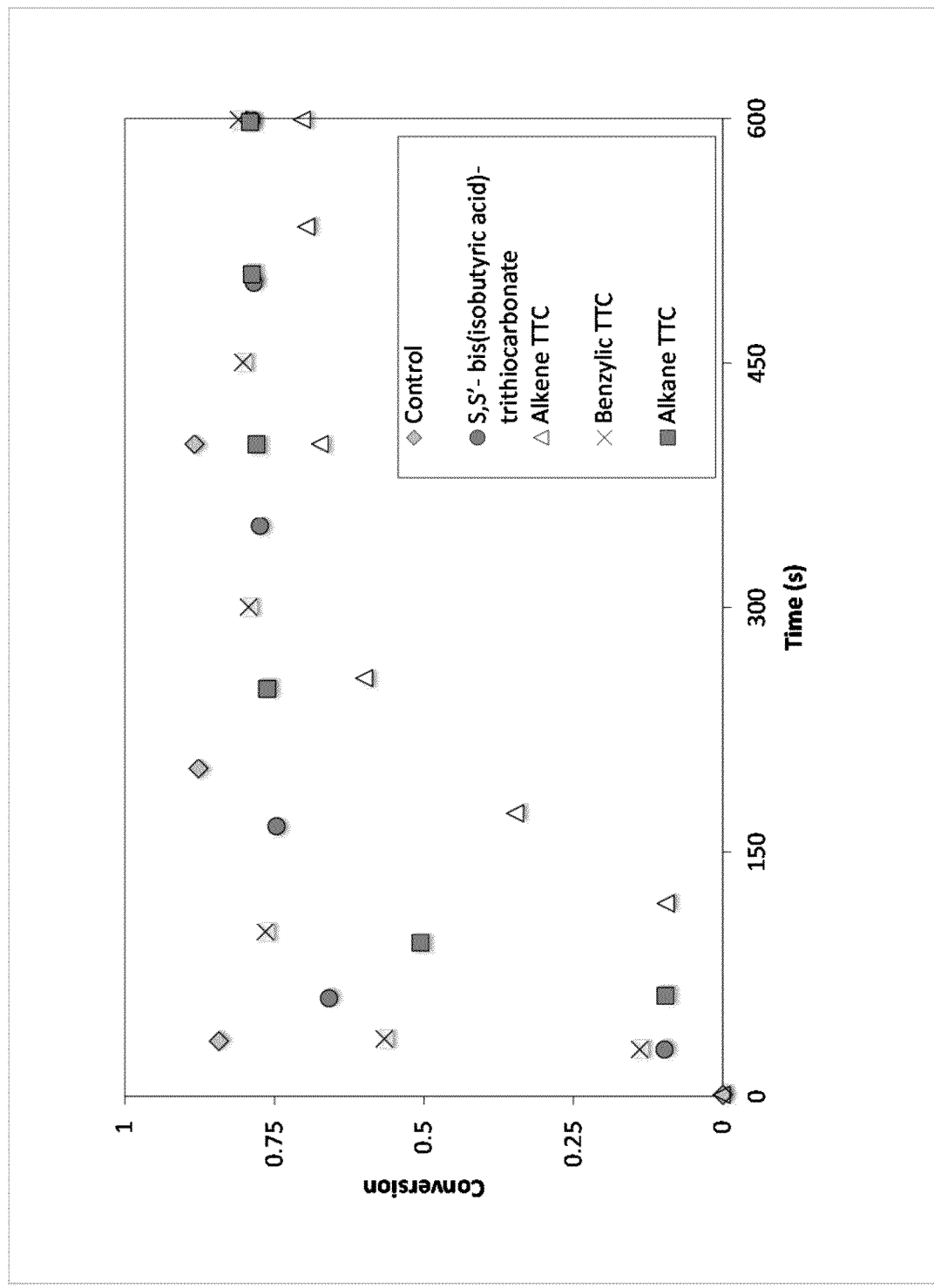
FIG. 9 is a graph illustrating trithiocarbonate chain-growth polymerization kinetics for various materials relative to Example 3. Samples were formulated with 70 wt % bisphenol A ethoxylated diacrylate, 28.5-20 wt % tetraethylene glycol diacrylate, diluted by varying the weight percent to the overall monomer formulation with the trithiocarbonate diacrylates as follows: 10% alkane, 5% S,S'-bis(isobutyric acid)-trithiocarbonate, 1.5% alkene, 2.0% benzyl, and control. All resins contained 0.25% DMPA as photoinitiator and were irradiated at 5 mW/cm$^2$ at 365 nm for 10 minutes.

The chain-growth system contained 70 wt % Bisphenol A ethoxylated diacrylate, 28.5-20 wt % Tetraethylene glycol diacrylate, and 10-1.5 wt % of the trithiocarbonate CRAFT monomers. The CRAFT concentrations were selected so that the rate retardation observed due to the CRAFT monomers did not alter the overall conversion of the polymerization below 70% conversion (FIG. 9).

Figure 10:
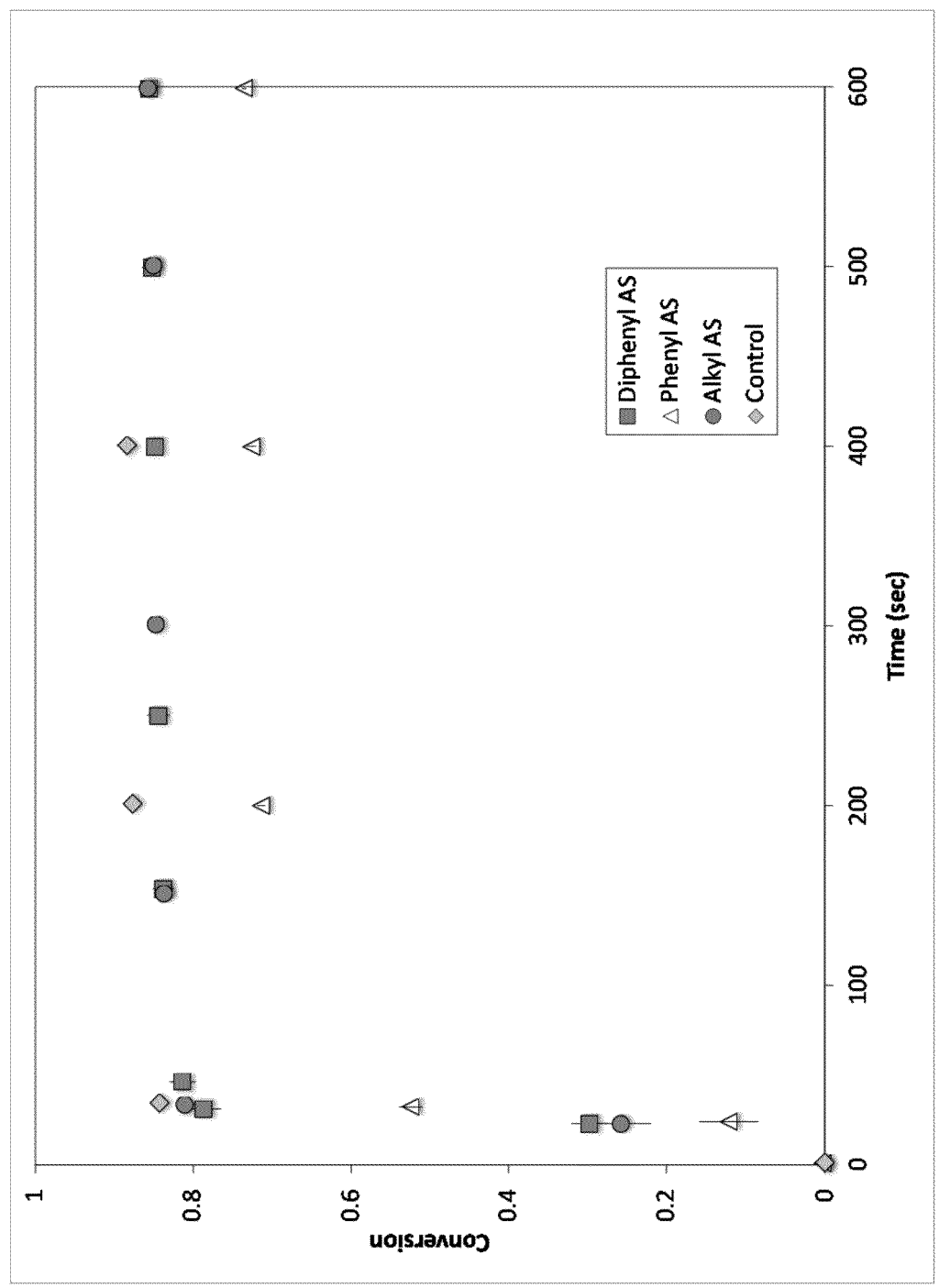
FIG. 10 is a graph illustrating allyl sulfide chain-growth polymerization kinetics for various materials relative to Example 3. Samples were formulated with 70% bisphenol A ethoxylated diacrylate, 20% tetraethylene glycol diacrylate, and 10% by weight of the corresponding alkyl allyl sulfide, phenyl allyl sulphide, diphenyl allyl sulphide, and control. All resins contained 0.25% DMPA as photoinitiator and were irradiated at 5 mW/cm$^2$ at 365 nm for 10 minutes.
Figure 11A:
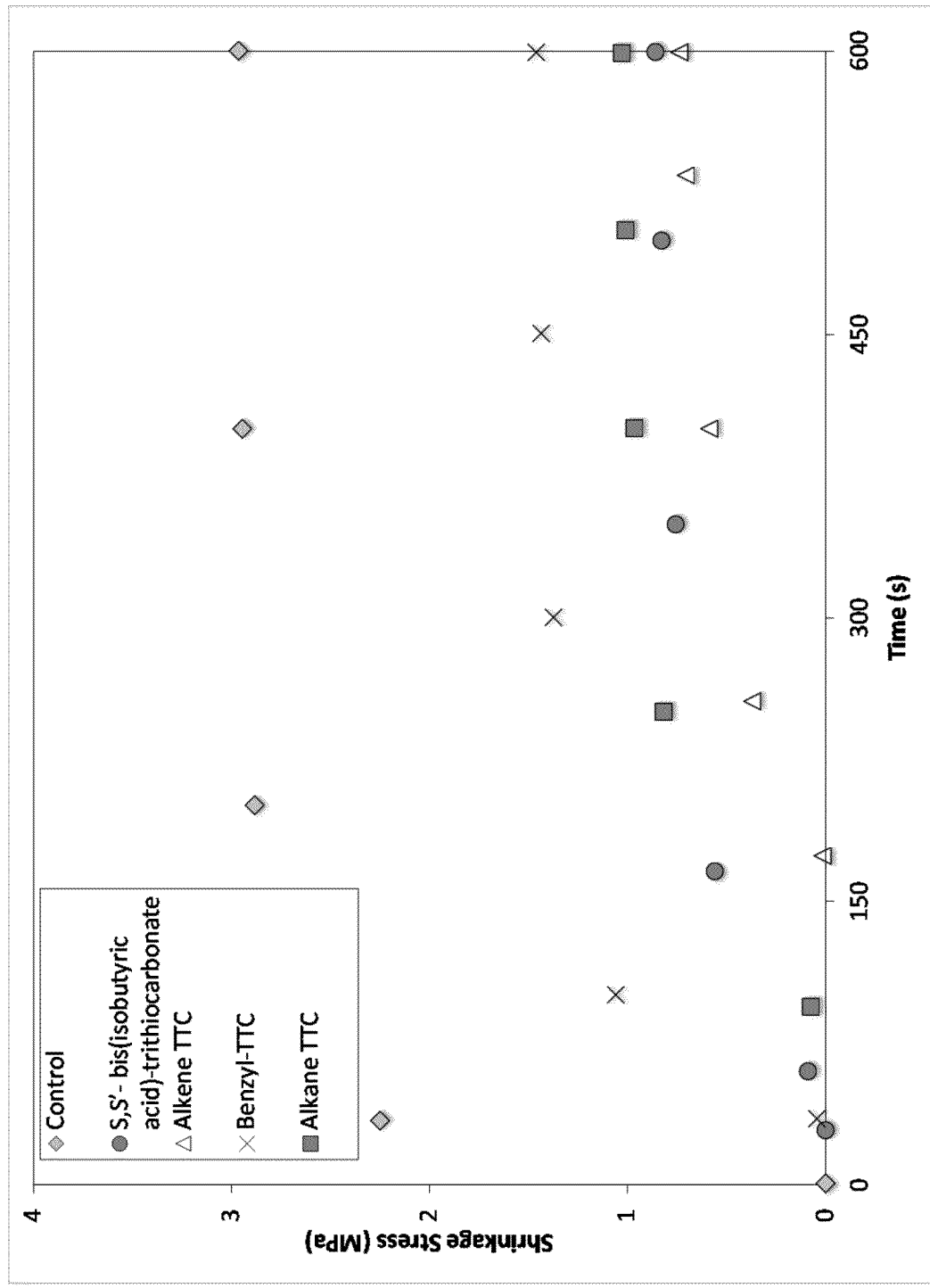
FIGS. 11(A), 11(B), 11(C) illustrate stress evolution over time, conversion of monomer over time, and stress evolution over conversion, respectively, relative to Example 3. Samples were formulated with 70 wt % bisphenol A ethoxylated diacrylate, 28.5-20 wt % tetraethylene glycol diacrylate, diluted by varying the weight percent to the overall monomer formulation with the trithiocarbonate diacrylates as follows: 10% alkane, 5% S,S'-bis(isobutyric acid)-trithiocarbonate, 1.5% alkene, 2.0% benzyl, and control. All resins contained 0.25% DMPA as photoinitiator and were irradiated at 5 mW/cm$^2$ at 365 nm for 10 minutes.
Figure 11B:
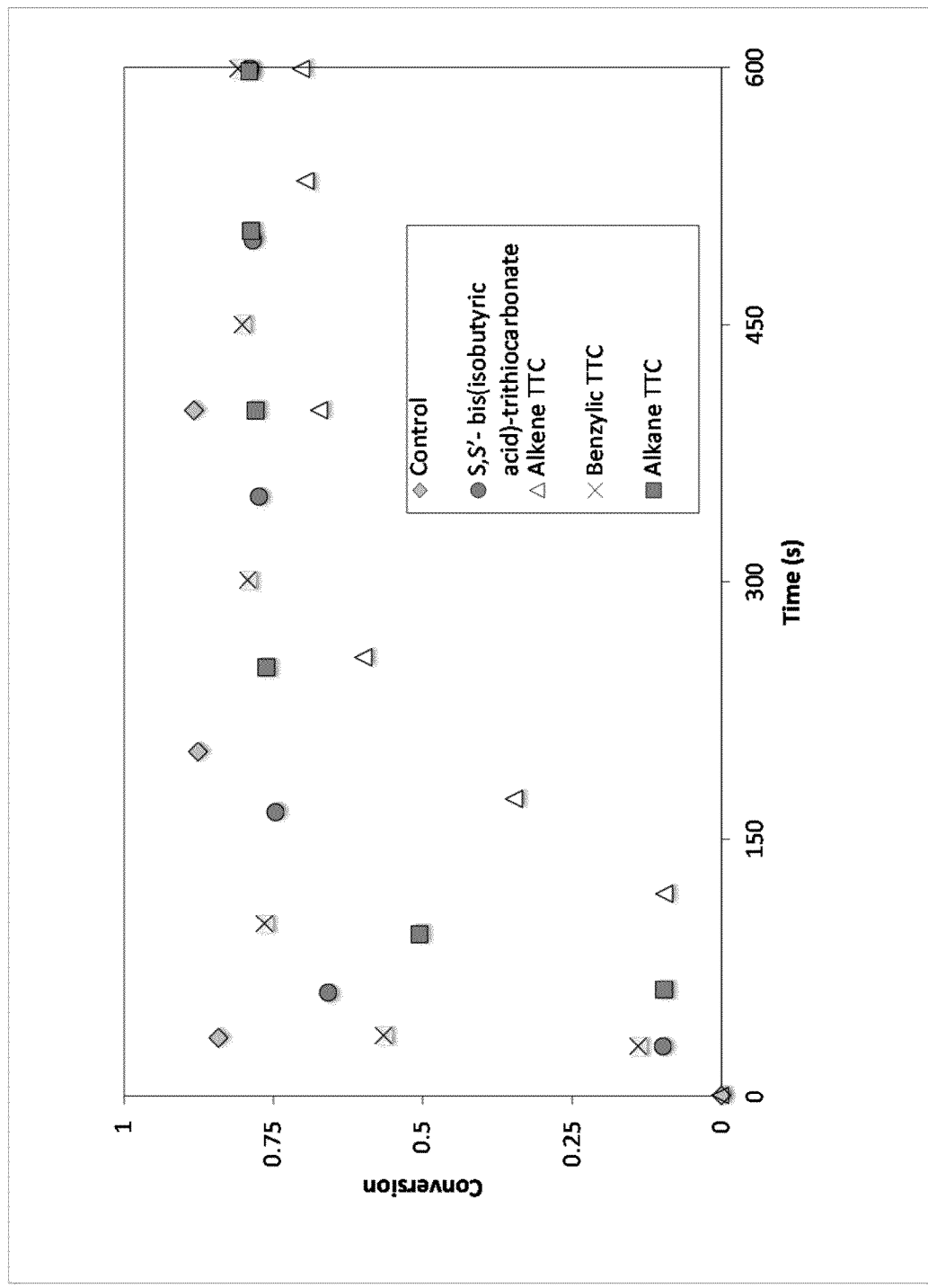
Figure 11C:
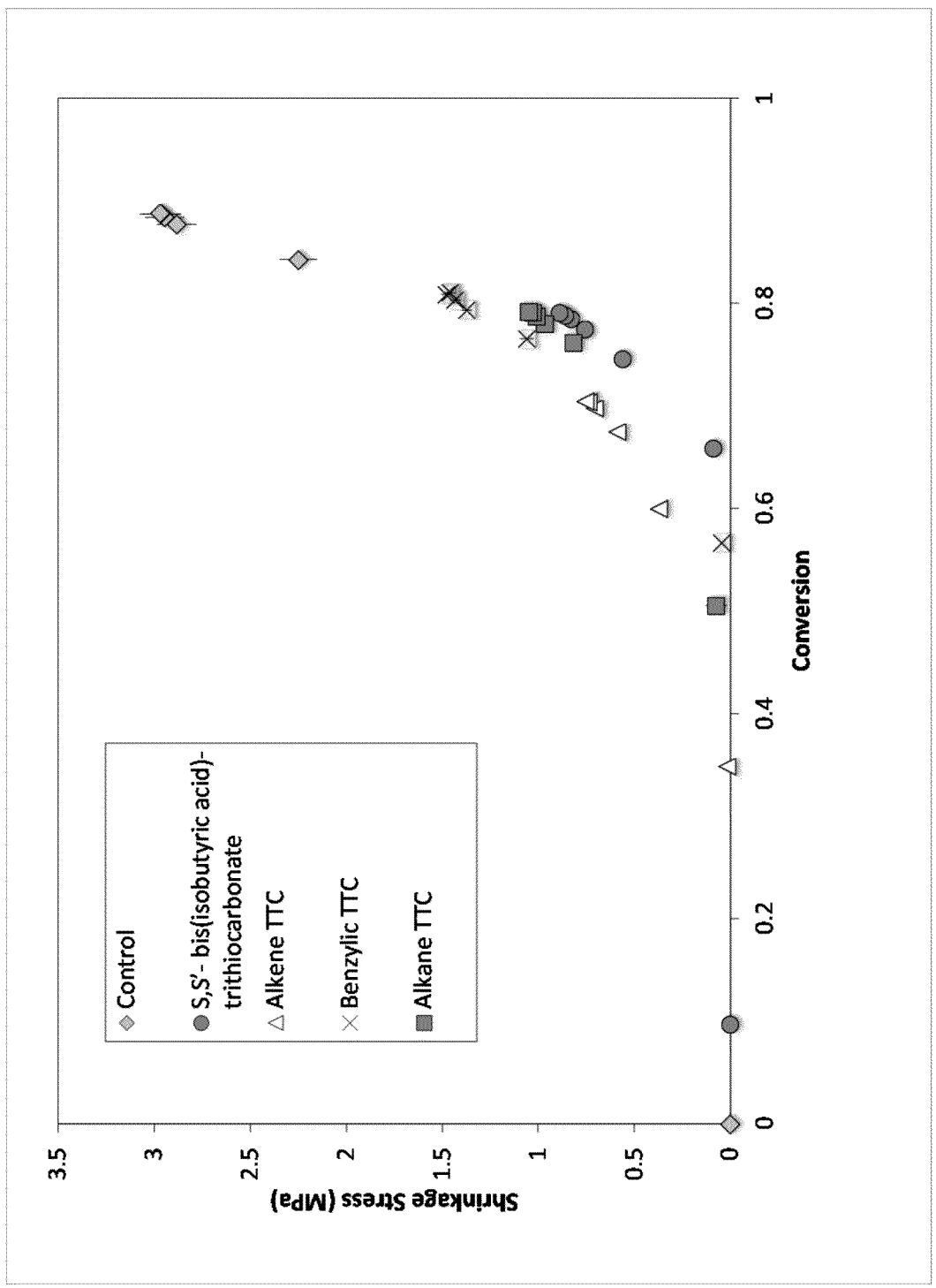
Figure 12A:
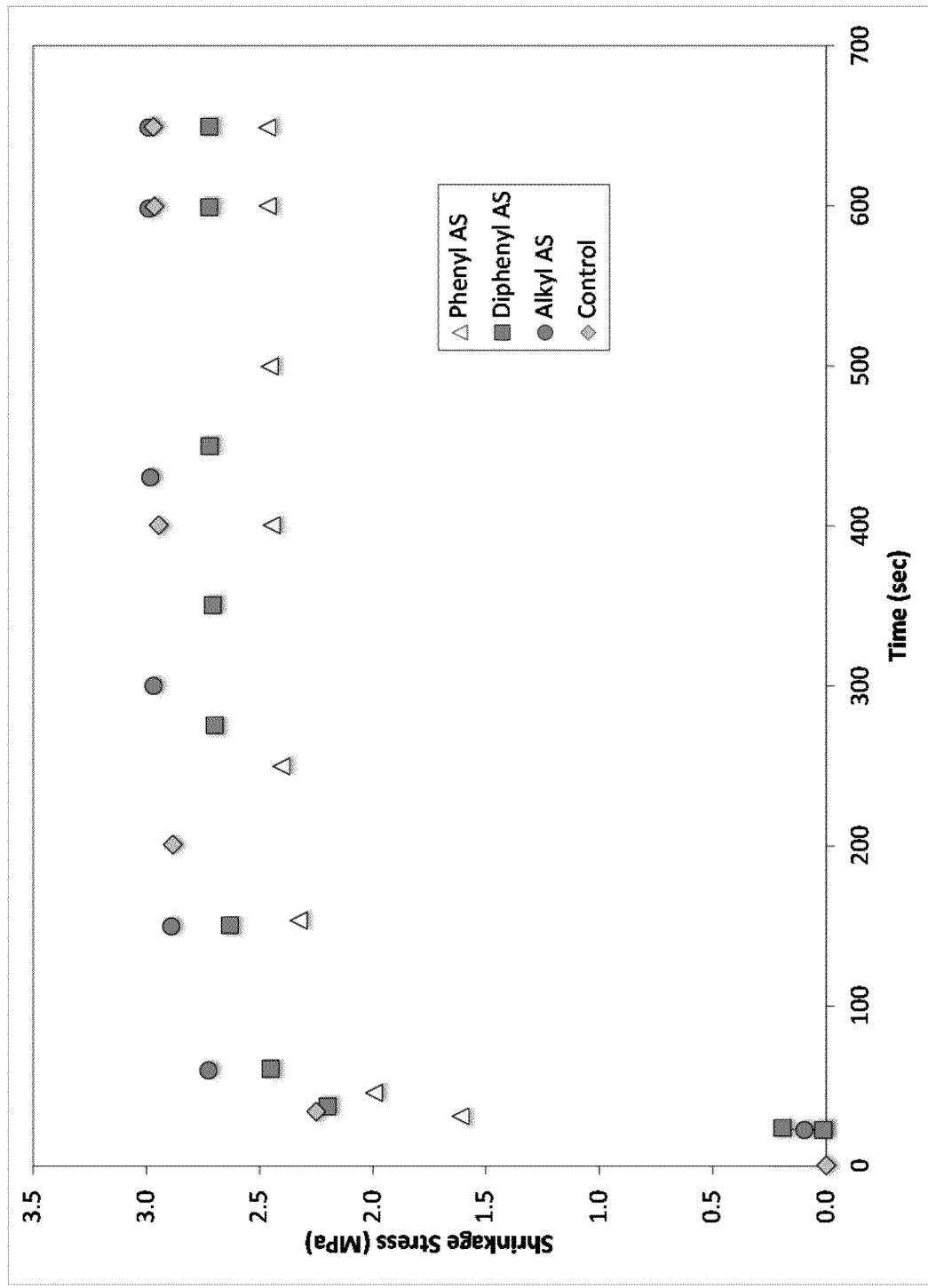
FIGS. 12(A), 12(B), and 12(C) illustrate stress evolution over time, conversion of monomer over time, and stress evolution over conversion, respectively, relative to Example 3. Samples were formulated with 70% bisphenol A ethoxylated diacrylate, 20% tetraethylene glycol diacrylate, and 10% by weight of the corresponding alkyl allyl sulfide, phenyl allyl sulphide, diphenyl allyl sulphide, and control. All resins contained 0.25% DMPA as photoinitiator and were irradiated at 5 mW/cm$^2$ at 365 nm for 10 minutes.
Figure 12B:
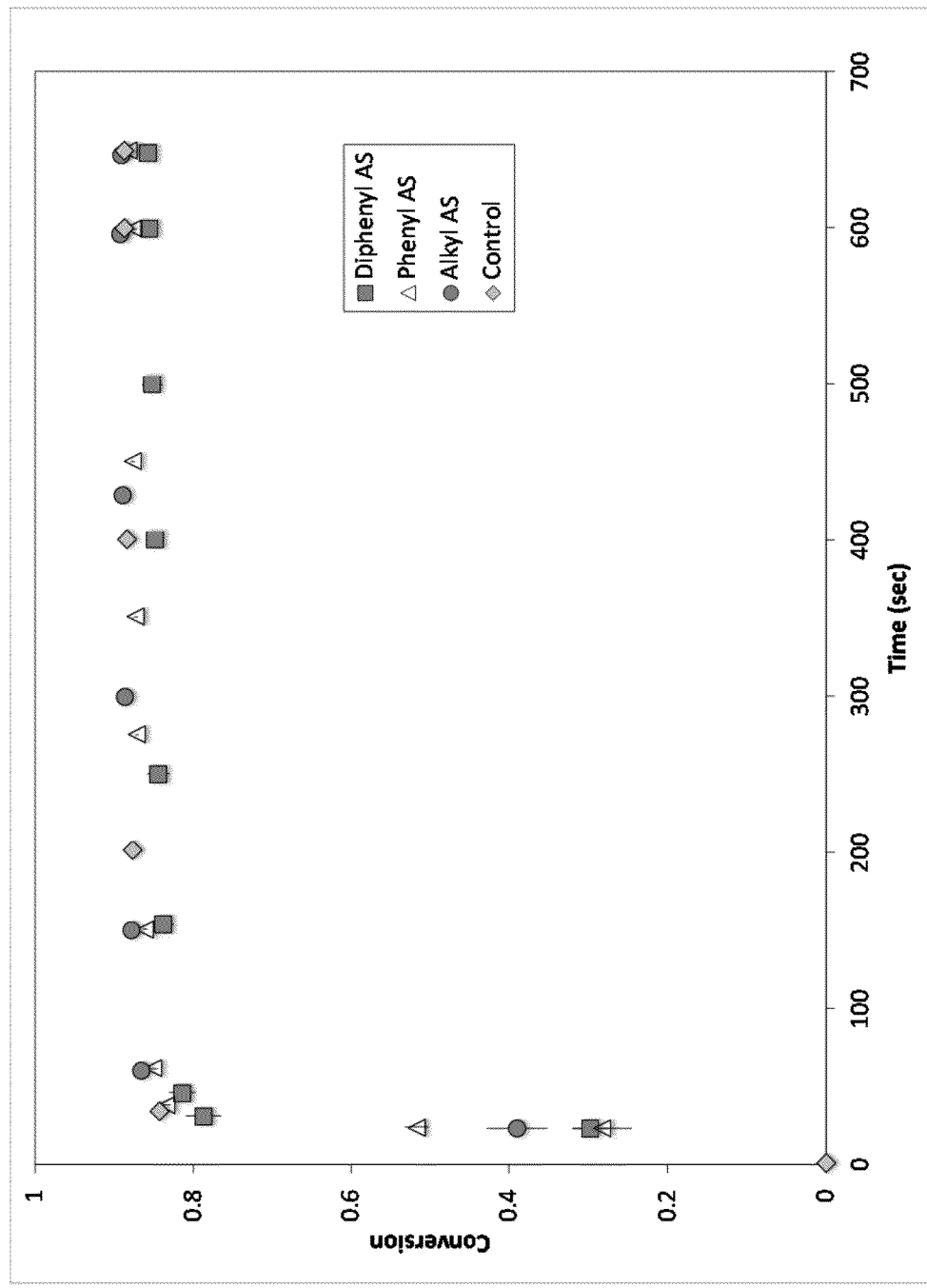
Figure 12C:
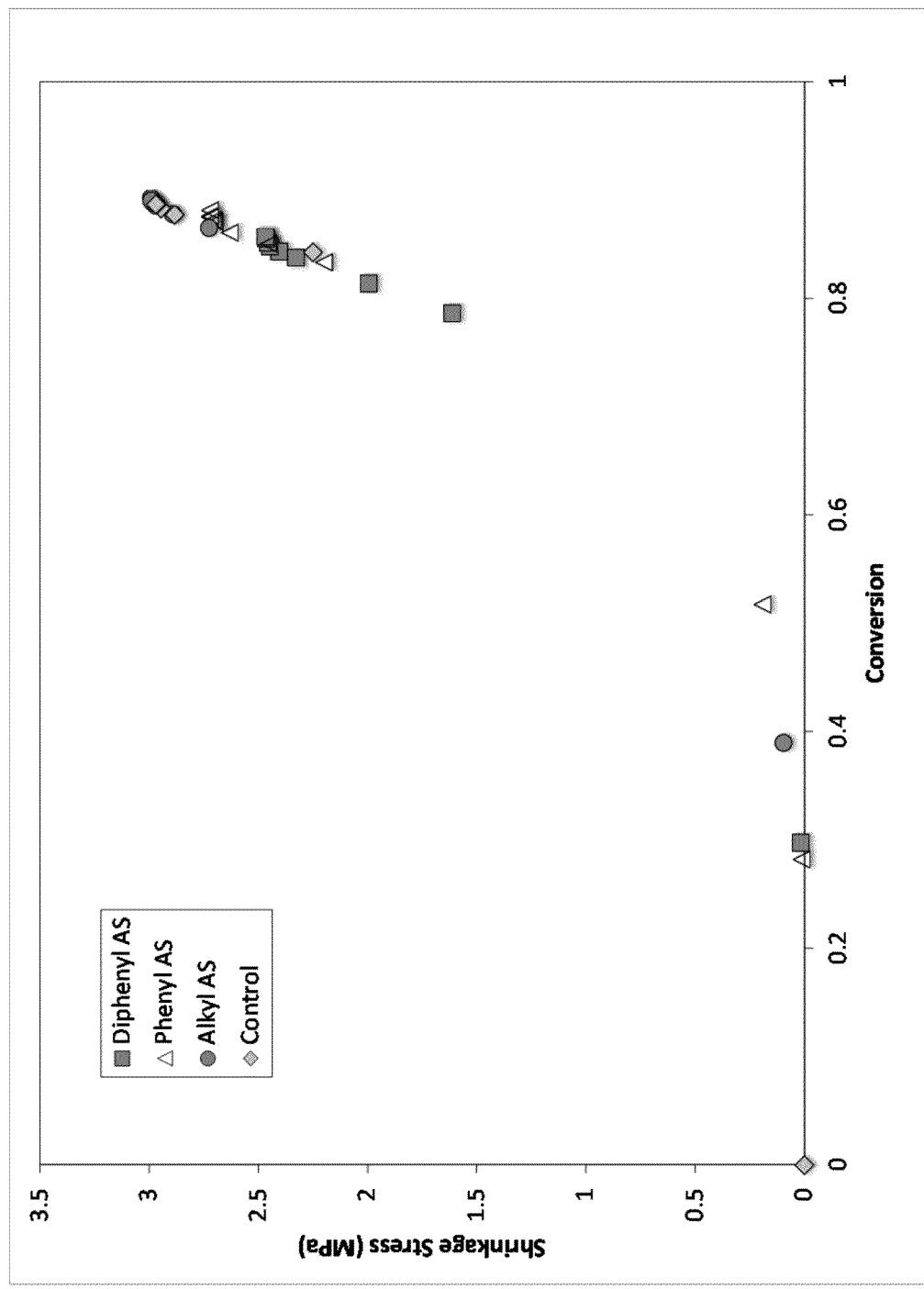
Figure 13A:
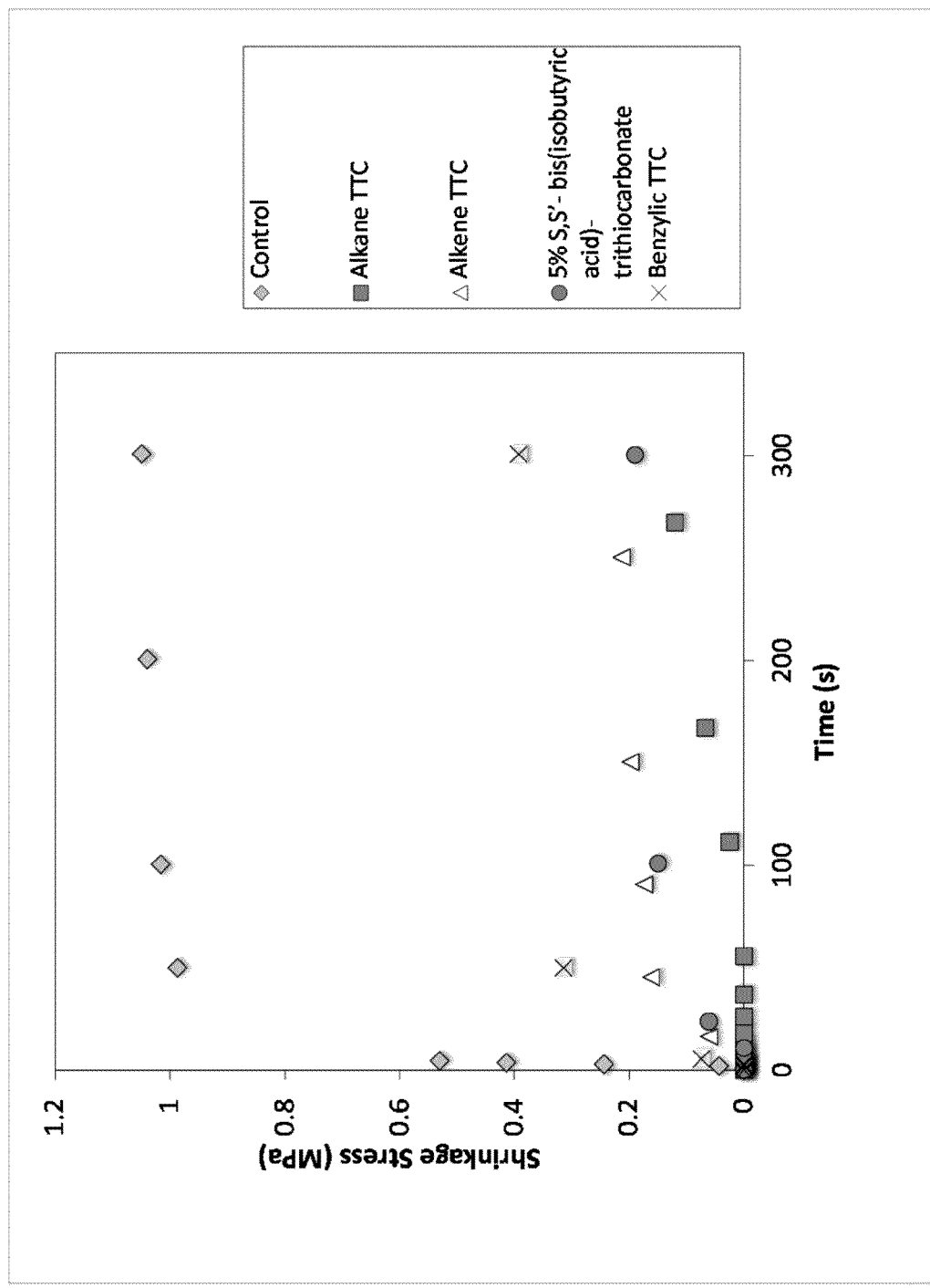
FIGS. 13(A), 13(B), and 13(C) illustrate stress evolution over time, conversion of monomer over time, and stress evolution over conversion, respectively, relative to Example 4. Samples were formulated with a 3:1 acrylate:thiol ratio based on the moles of functional groups from bisphenol A ethoxylated diacrylate/PETMP diluted by varying the weight percent to the overall monomer formulation with the trithiocarbonate diacrylates as follows: 10% alkane, 5% S,S'-bis (isobutyric acid)-trithiocarbonate, 1.5% alkene, 2.0% benzyl, and the control with no trithiocarbonate. All resins contained 0.25% DMPA as the photoinitiator and were irradiated at 5 mW/cm$^2$ at 365 nm for 10 minutes.
Figure 13B:
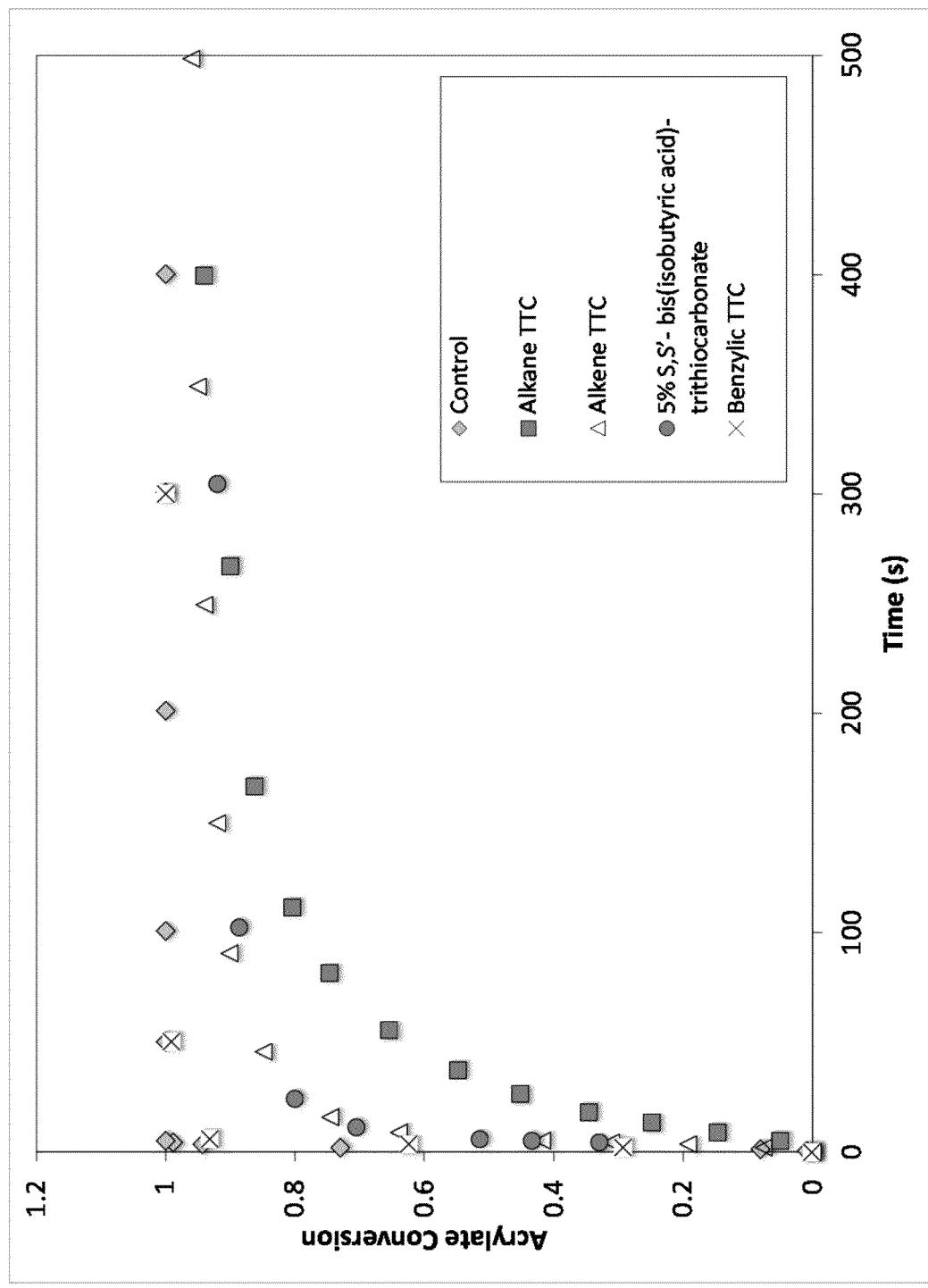
Figure 13C:
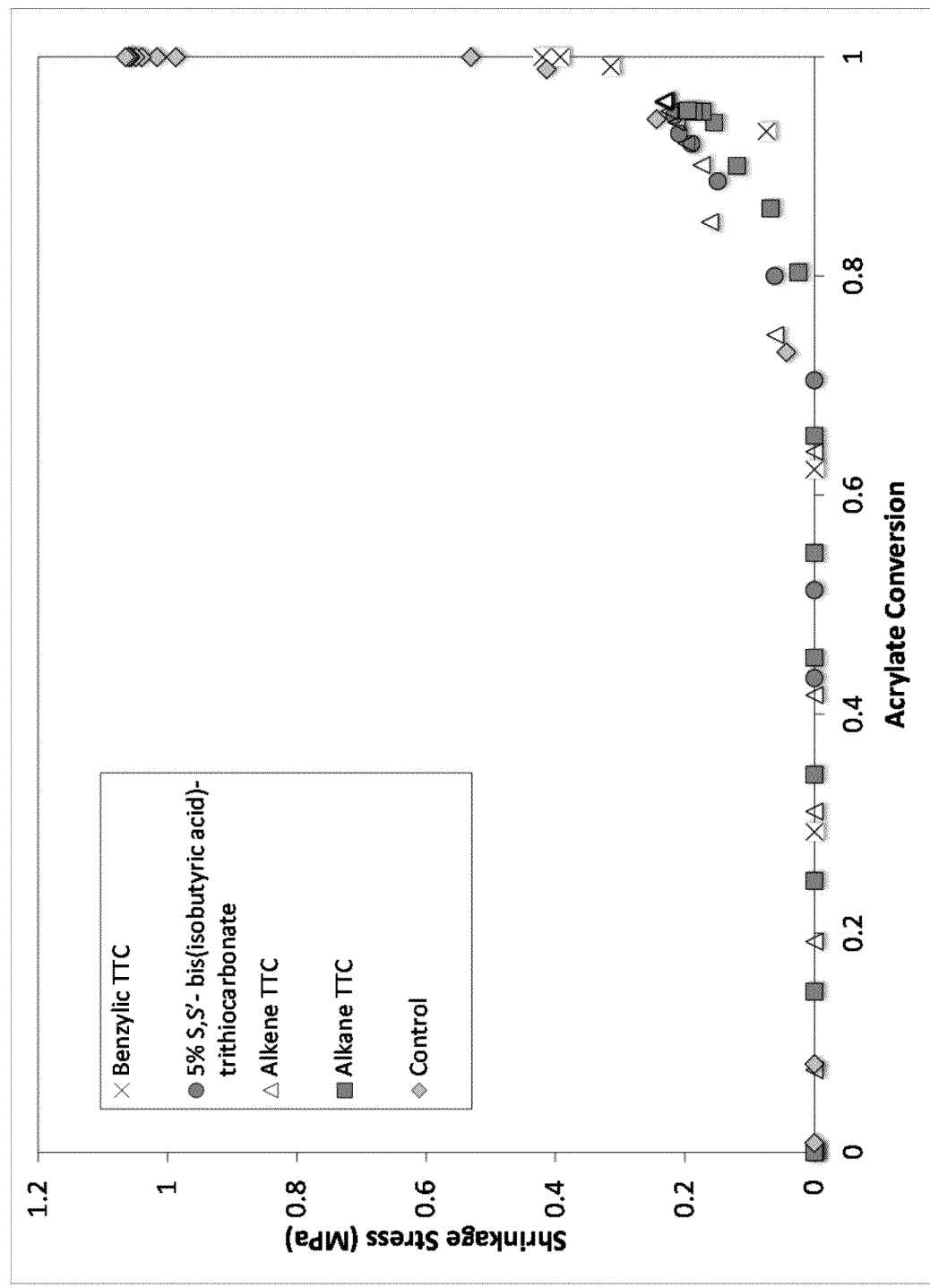
Figure 14A:
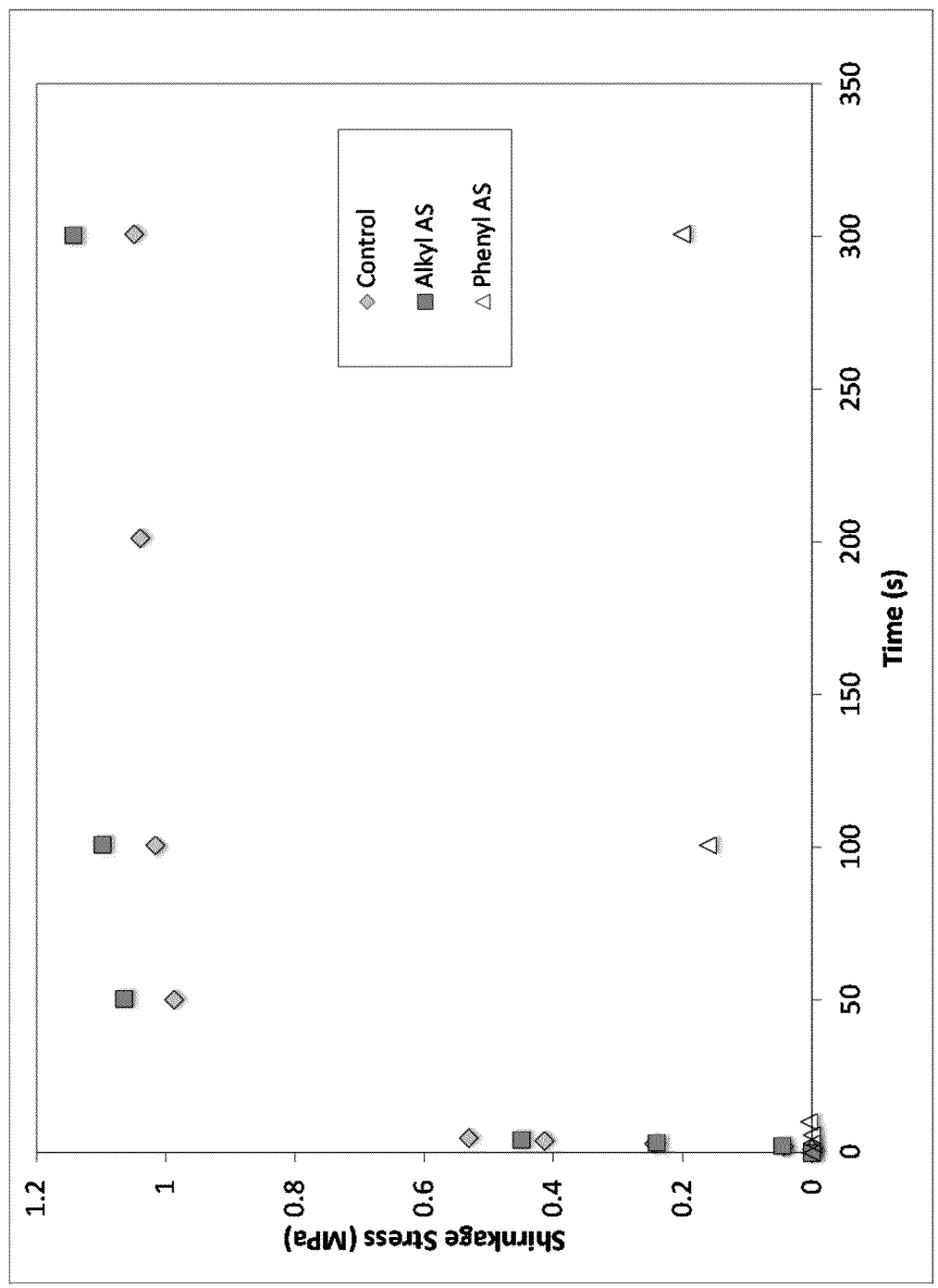
FIGS. 14(A), 14(B), and 14(C) illustrate stress evolution over time, conversion of monomer over time, and stress evolution over conversion, respectively, relative to Example 4. Samples were formulated with a 3:1 acrylate:thiol ratio based on the moles of functional groups comprised of bisphenol A ethoxylated diacrylate/PETMP with 10% by weight to the overall monomer formulation of the allyl sulfides as follows: 10% alkyl allyl sulfide diacrylate, 10% phenyl allyl sulphide diacrylate, and the control with no CRAFT monomer. All resins contained 0.25% DMPA as photoinitiator and were irradiated at 5 mW/cm$^2$ at 365 nm for 10 minutes.
Figure 14B:
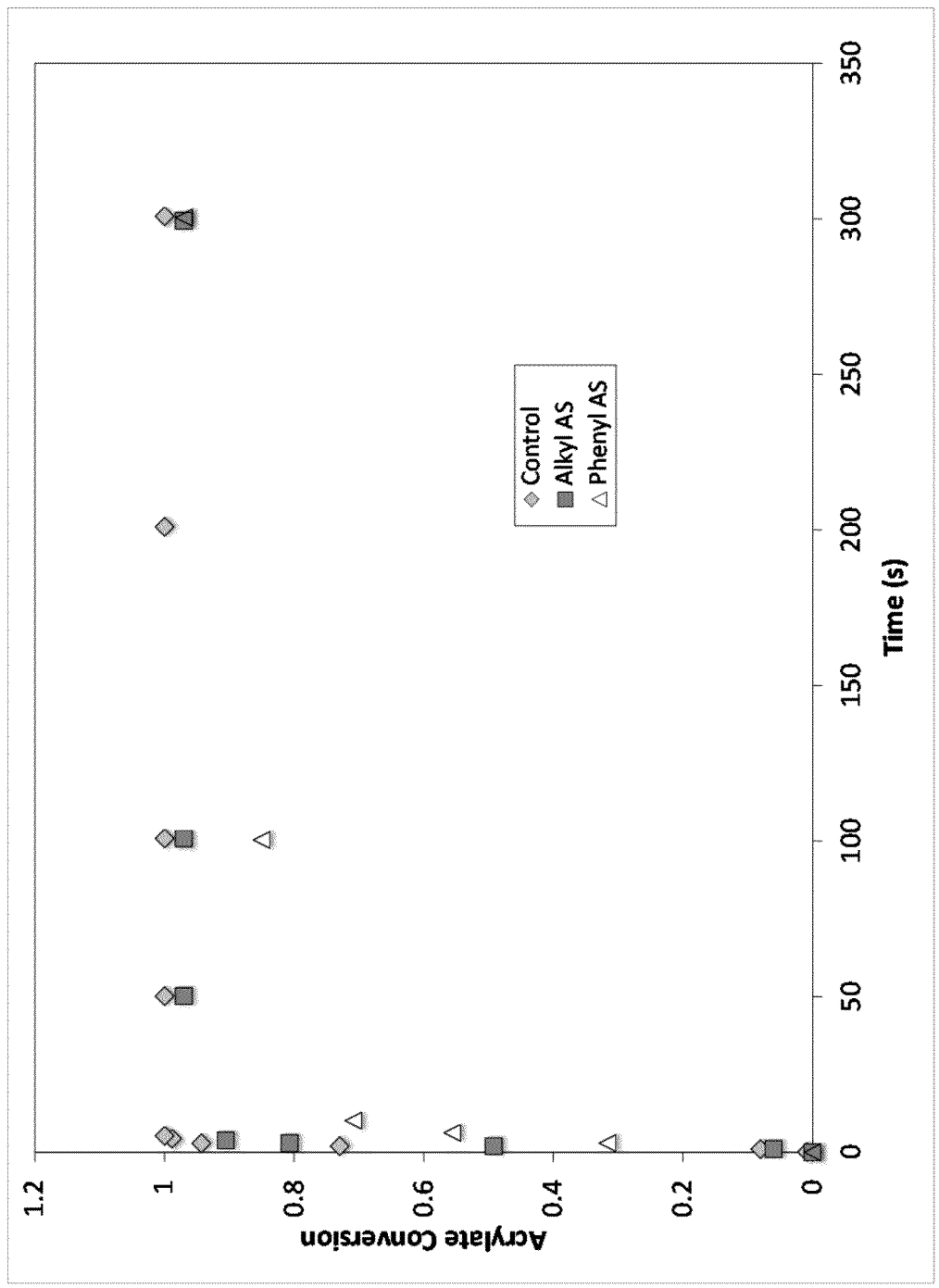
Figure 14C:
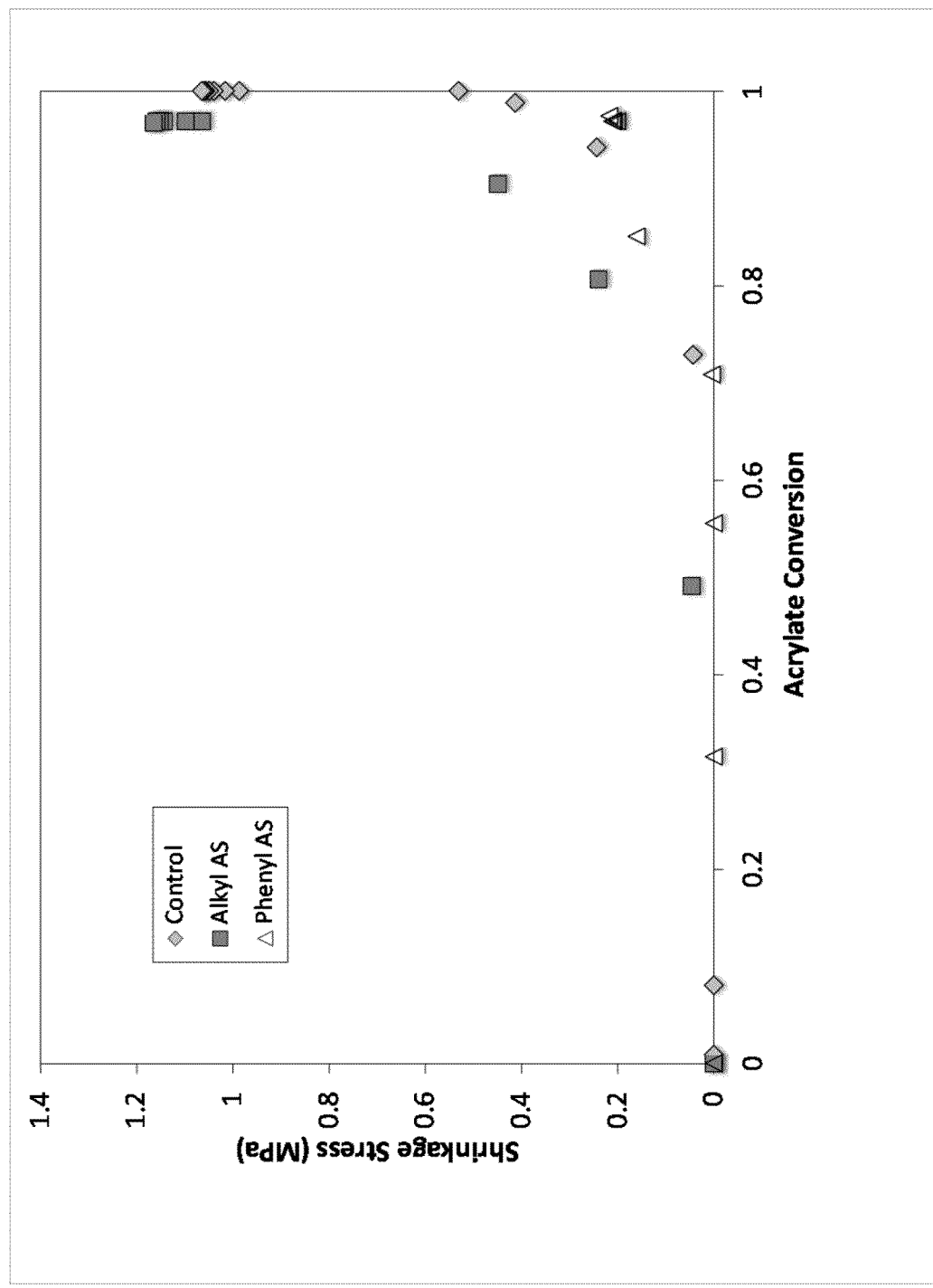
Figure 15A:
FIGS. 15*a*-15*e* illustrate some chemical compounds that may be used as the core unit, the linker units, and the end units.
Figure 15B:
Figure 15C:
Figure 15D:
Figure 15E:
Figure 16:
FIG. 16 illustrates an acrylate compound that may be used as an end group (unit).

The allyl sulfide CRAFT monomers were formulated in the same networks as the trithiocarbonate monomers. It is well known that the allyl sulfide containing compounds are non-reversible. After the two central sulfur atoms have been released during the chain transfer process, the compounds reach an equilibrium with the surrounding monomers, and the chain transfer process no longer dictates the polymerization process. Due to the lack of reversibility of the AFT allyl sulfides, the allyl sulfide monomers were incorporated in concentrations of 10 wt % in the chain-growth polymerization experiments (FIG. 10). In FIG. 10 the control was the monomer solution that contained strictly the acrylate monomers with no RAFT component.

Without wishing to be bound by any particular belief, we believe the unique rate retardation properties of the CRAFT monomer in the acrylate chain-growth polymerizations are due to two major factors. The first factor relates to the stability of the radical leaving group. This has been described by Thang and co-workers as the $K_\beta$.[3] The rate of β-scission of the intermediate to generate the leaving radical, (R), is a factor in the control of the polymerization rate. The linker incorporated into each monomer was chosen specifically to affect the stability of the leaving radical. The more stable the leaving radical the greater the chain transfer properties of the monomer. Secondly, the efficiency of the leaving radical, (R), to attack another trithiocarbonate radical and facilitate the chain transfer process is also believed to be a factor.

As predicted, the trithiocarbonates with their ability to have fully reversible AFCT show the greatest reduction in shrinkage stress during an in-situ polymerization. The trithiocarbonates by rate retardation are able to control the amount of stress relaxation extremely efficiently in the chain polymerizations. The alkene trithiocarbonate showed the greatest stress relaxation with only 1.5% bw (by weight) loading. In the chain polymerization, the alkene trithiocarbonate was able to reduce stress evolution by 77%. The allyl sulfides were not as efficient in reducing stress evolution in chain polymerization. This can be explained by the inability of the allyl sulfides to be completely reversible AFCT agents and that the attack of the thiyl radical on carbon centers is not as efficient. The best allyl sulfide was the phenyl allyl sulfide that showed 50% stress reduction at 10% bw loading in the monomer formulation.

The newly synthesized CRAFT monomers were subsequently evaluated in their ability to reduce stress evolution during in-situ polymerization. The monomers ability to reduce stress evolution were evaluated by a tensometer. FIGS. 11A-11B and 12A-12B show results for shrinkage stress over time and conversion over time for trithiocarbonate monomers and allyl sulfide monomers, respectively (the control was the monomer mixture with no RAFT component).

EXAMPLE 4

Incorporation of Monomers into Polymer Networks by Mixed Mode Polymerization

The newly synthesized CRAFT monomers were also evaluated in their ability to reduce stress evolution during mixed-mode polymerization. The monomers ability to reduce stress evolution were evaluated by a tensometer. FIGS. 13A-13B and 14A-14B show results for shrinkage stress over time and conversion over time for trithiocarbonate monomers and allyl sulfide monomers, respectively (the control was the monomer mixture with no RAFT component).

The trithiocarbonates by rate retardation are able to control the amount of stress relaxation extremely efficiently in the chain-step polymerizations. The alkene trithiocarbonate showed the greatest stress relaxation with only 1.5% bw loading. In the chain-step growth polymerization, the alkene trithiocarbonate was able to reduce stress evolution by 82%. In the mixed mode (chain-step growth) polymerization, the allyl sulfides perform much better as AFCT agents. The introduction of PETMP allows for thiyl radicals to have a greater affinity for the allyl sulfides and increase their ability to be reversible and promote chain transfer. The phenyl allyl sulfide was able to reduce the stress by 82% with a 10% loading in the mixed mode monomer formulation.

Additional Experimental Details

Methods and Equipment: The shrinkage stress and functional group conversion were simultaneously observed during polymerization using a tensometer coupled with a FTIR (Nicolet 670), which was equipped with near-infrared transmitting optical fiber patch cables and an indium gallium arsenide (InGaAs) detector. The tensometer was developed by the Paffenbarger Research Center (American Dental Association Health Foundation) to measure the stress during photopolymerization. Stress evolution is measured by the cantilever beam deflection that is detected by the LVDT (linear variable displacement transducer). In the tensometer, one glass rod is fixed to the bottom plate and another rod is connected to the cantilever beam. The formulated resin was injected between the two glass rods, which results in a specimen geometry of 6 mm diameter and 1 mm thickness. Samples were irradiated with 365 nm filtered UV light at 5 mW/cm2 (Acticure 4000, EXPO) for 10 min. Evolution of the acrylate and methcrylate double bond concentrations were determined by monitoring the infrared absorption peaks centered at 6200 cm-1 (C=C—H stretching, overtone).

The post polymerization stress relaxation studies, the elastic moduli (E') and glass transition temperatures (Tgs) of polymerized samples were measured by dynamic mechanical analysis (DMA, TA Instruments Q800) (Table 2). For post polymerization stress relaxation studies, specimens (10 mm×3 mm×0.5 mm) for DMA were prepared and strained at a rate of 0.5N/min until a constant strain of 10.0N was achieved. The samples were held for 2 minutes to alleviate any viscoelastic creep in the networks. Following the two minutes hold, the samples were irradiated for 30 minutes using 365 nm light at 20 mW/cm$^2$. The samples were restrained to 15.0N to ensure there were no viscoelastic or cross-linking changes in the network.

NMR spectra were acquired on a Bruker AVANCE-III 400 NMR Spectrometer system operating at 400.13 MHz for 1H observation. Solvent chemical shifts were referenced through Mesternova from J. Org. Chem. 1997, 62, 7512-7515.

The UV-Vis was employed using a diode array double-beam spectrophotometer with Ebert monochromator (Evolution 300, Thermo-Scientific, West Palm Beach, Fla.). Absorption spectra were collected in quartz cuvettes with a 1 cm pathlength. Mass Spectrometry was done on a Synapt G2 High Definition Mass Spectrometer (Waters Company).

The ESI-MS settings are as follows: capillary voltage: 2.8 kV (positive mode), −2.2 kV (negative mode); sampling cone voltage: 20-40V depending on the molecular weight. (The higher the mw, the higher the sampling cone); extraction cone: 4.0V; Source temperature: 80° C.; desolvation temperature: 150° C.; desolvation gas (N2): 600 L/h 2. The samples were scanned for molecular ion analysis using ESI by dissolving or diluting the sample in MeOH or MeOH/DCM (50:50), and infusing the sample in Q-TOF MS with 5 uL/min flow rate to acquire the data.

Experimental Section: Materials: 3-Chloro-2-chloromethyl-1-propene, mercaptoethanol (99%), 3-(tert-butyl)dimethyl silyl-1-bromopropane, 4-bromocrotonoate, DIBAL-H, diethyl azodicarboxylate, triphenylphosphine, TBDMSCI, imidazole, tetrabutyl ammonium fluoride, glacial acetic acid, 4-hydroxythiophenol, 4-iodoanisol, 4-bromothioanisole, triethylamine (>99%), acryloyl chloride, sodium metal (99%) and ethylene glycol dimercaptopropoinate (EGDMP), tetraethylene glycol diacrylate, (TEGDA), carbon disulfide, potassium carbonate, N,N-di-methylformamide, acetonitrile, N,N-dimethyl acetamide, hexanes, ethyl acetate, methanol, dry tetrahydrofuran (99.5%), dry dichloromethane (99.5%), p-chlorobenzyl chloride, and all other chemicals unless specified were obtained from Sigma Aldrich. Pentaerythritol tetrakis (3-mercaptopropionate), (PETMP), was obtained from Evans Chemetics. Irgacure 651 (2,2-Dimethoxy-2-phenylacetophenone-DMPA were obtained from BASF (formally Ciba). All chemicals were used without further purification.

Compound 1: To a solution of dry DMF (100 mL=1M solution concentration) under $N_2$ and degassed for 30 minutes was added potassium carbonate (14.5 g, 105 mmol) and carbon disulfide (8.37 g, 110 mmol). The reaction was stirred vigorously for 15 minutes. The solution turned a deep blood-red color. To the solution was added 3-(tert-butyl)dimethyl silyl-1-bromopropane (26.5 g, 105 mmol), and the reaction turned an immediate yellow color. The reaction was heated to 40 C for 24 hours. The reaction showed 40% conversion by NMR analysis. To the reaction was added another 0.5 eq of carbon disulfide. The reaction was monitored by NMR, and over time small portions of $CS_2$ and $K_2CO_3$ were added until the reaction was complete by NMR. A total of 2.5 eq of carbon disulfide and 1.5 eq of potassium carbonate were added to the reaction. The reaction was quenched with 250 mL of water and taken up in ethyl acetate (500 mL). The organic layer was washed with water (250 mL×3) and brine (250 mL). The organic layer was dried over sodium sulfate, filtered, and reduced in vacuo to yield a crude yellow oil. The oil was purified by flash chromatography in a gradient fashion 100% hexanes to 99:1 hexanes/ethyl acetate to yield 22.18 g of pure product. Yield 93%. $^1$H NMR (400 MHz, $CDCl_3$, δ): 3.69 (t, J=8 Hz, 4H), 3.45 (t, J=8 Hz, 4H), 1.91 (p, J=8 Hz, 4H), 0.90 (s, 18H), 0.06 (s, 12H); $^{13}$C NMR (400 MHz, $CDCl_3$, δ): 224.63 (C=S), 61.62 (C4), 33.62 (C2), 31.23 (C3), 26.08 (C7), 18.45 (C6), 5.19 (C5); MS (ESI, m/z): [M+Na]$^+$ calcd for $C_{19}H_{42}O_2S_3Si_2$, 477.2; found, 477.2.

Compound 2: To a solution of the silyl-protected alkyl trithiocarbonate (22.18 g, 48.75 mmol) in THF (487 mL=0.1M) at 0 C under $N_2$ was added AcOH (6.44 g, 2.2 eq) and TBAF (107 mL, 107 mmol). The reaction was allowed to warm up to RT overnight. After 24 hrs, the reaction was reduced in vacuo, and the organic layer was taken up in 500 mL of ethyl acetate. The organic layer was washed with water (250 mL×3) and brine (250 mL). The organic layer was dried over sodium sulfate, filtered, and reduced in vacuo to yield a crude yellow oil. The oil was purified by flash chromatography in a gradient fashion 40%:60% ethyl acetate/hexanes to 60:40 ethyl acetate/hexanes to afford 7.12 g of a pure yellow oil. Yield 65%. $^1$H NMR (400 MHz, $CDCl_3$, δ): 3.70 (t, J=8 Hz, 4H), 3.48 (t, J=8 Hz, 4H), 2.28 (s, OH, 2H), 1.94 (p, J=8 Hz, 4H); $^{13}$C NMR (400 MHz, $CDCl_3$, δ): 225.25 (C=S), 61.04 (C4), 33.43 (C2), 31.19 (C3); MS (ESI, m/z): [M+Na]$^+$ calcd for $C_7H_{14}O_2S_3$, 249.0; found, 249.0.

Compound 3: To a solution of Compound 2 (5.0 g, 22.1 mmol) in THF (220 mL) was added triphenylphosphine (20.27 g, 77.3 mmol) and acrylic acid (5.3 mL, 3.5 eq). The solution was cooled to 0 C and placed under $N_2$. To the reaction was added 40% DEAD (35.21 mL, 3.5 eq) dropwise. After 1 hour, the reaction was warmed to 25 C and allowed to stir 16 hours. The reaction was diluted with hexanes and cooled to 0 C to precipitate the triphenylphosphine oxide bi-product. The reaction was filtered and reduced in vacuo to a crude yellow oil. The oil was purified by flash chromatography in a gradient fashion using 100% hexanes to 85:15 hexanes/ethyl acetate to afford 6.52 g of the product. Yield 89%. $^1$H NMR (400 MHz, $CDCl_3$, δ): 6.42 (dd, 2H), 6.13 (dd, 2H), 5.85 (dd, 2H), 4.24 (t, J=8 Hz, 4H; $CH_2$), 3.46 (t, J=8 Hz, 4H; $CH_2$), 2.09 (p, J=8 Hz, 4H, $CH_2$); $^{13}$C NMR (400 MHz, $CDCl_3$, δ): 223.47 (C=S), 166.15 (C5), 131.18 (C7), 128.36 (C6), 63.04 (C4), 33.33 (C2), 27.66 (C3); UV-vis (methanol): $\lambda_{max}(\epsilon)$=430 nm (27000); MS (ESI, m/z): [M+Na]$^+$ calcd for $C_{13}H_{18}O_4S_3$, 357.0; found, 357.0.

Compound 4: The following molecule was synthesized from either 4-bromocrotonoate or methyl trans-4-bromo-2-butenoate. To 4-bromocrotonoate (25 g, 139.66 mmol) in a solution of diethyl ether (500 mL) at −78 C under $N_2$ was added 1M DIBAL-H in hexanes (350 mL, 2.5 eq). The DIBAL-H was added through an addition funnel dropwise over 3-4 hrs. The reaction was warmed to 0 C, and the reaction was stirred for an additional hour before being quenched with 40 mL of AcOH. The reaction was warmed to RT and filtered over celite. The product was reduced in vacuo, and the crude yellow oil (appr. 22 g) was carried forward immediately to be TBDMS protected due to the instability of the intermediate.

To a solution of the 4-bromo-2-butenol (22 g, 145.69 mmol) and imidazole (19.84 g, 291.39 mmol) in DCM (730 mL) at 0 C under $N_2$ was added TBDMSCl (32.93 g, 1.5 eq) in 3 portions over 30 minutes. The reaction was allowed to warm up to room temperature overnight. After 12 hours, the reaction was complete by TLC. The reaction was filtered, washed with 1N HCl (1×100 mL), water (2×100 mL), brine (1×200 mL), and dried over sodium sulfate. The organic layer was filtered and reduced in vacuo to yield 32.4 g of a crude material. The crude was purified by FC using 100% hexanes to yield 23 g of the desired product. Yield 62%. $^1$H NMR (400 MHz, $CDCl_3$, δ): 5.89 (m, 2H), 4.21 (m, 2H), 3.98 (dt, 2H), 0.93 (s, 9H), 0.09 (s, 6H); $^{13}$C NMR (400 MHz, $CDCl_3$, δ): 134.63 (C3), 125.78 (C2), 62.57 (C4), 32.36 (C1), 25.91 (C7), 18.36 (C6), 5.26 (C5); MS (ESI, m/z): [M+H]$^+$ Hr calcd for $C_{10}H_{21}BrO_2Si$, 265.1; found, 265.1.

Compound 5: To a solution of silyl-protected bromo-alkene (26.84 g, 101.2 mmol) in N,N-dimethylacetamide (200 mL) was added carbon disulfide (15.42 g, 202.4 eq) and potassium carbonate (27.96 g, 202.4 mmol). The reaction was placed under inert atmosphere and heated to 40 C for 24 hours. The reaction was cooled to 25 C and quenched with water. The aqueous layer was extracted with methylene chloride. The organic layer was washed with water, brine, and dried over sodium sulfate. The organic layer was reduced in vacuo to a crude yellow oil. The oil was purified by flash chromatography 95:5 hexanes/ethyl acetate to yield 8.12 g of the silyl protected alkene trithiocarbonate. Yield 34%. $^1$H NMR (400 MHz, $CDCl_3$, δ): 5.79 (m, 4H), 4.15 (m, 4H), 4.03 (m, 4H), 0.90 (s, 18H), 0.06 (s, 12H); $^{13}$C NMR (400 MHz, $CDCl_3$, δ): 222.87 (C=S), 135.09 (C4), 122.57 (C3), 63.17 (C5), 38.88 (C2), 26.08 (C8), 18.54 (C7), 5.07 (C6); MS (ESI, m/z): [M+Na]$^+$ calcd for $C_{21}H_{42}O_2S_3Si_2$, 501.2; found, 501.2.

Compound 6: To a solution of the compound 5 (8.12 g, 16.98 mmol) in THF (200 mL) at 0 C under $N_2$ was added AcOH (3.0 mL, 50.94 mmol) and TBAF (43 mL, 42.5 mmol). The reaction was allowed to warm up to RT overnight. After 16 hrs, the reaction was reduced in vacuo to yield a crude yellow oil. The oil was purified by flash chromatography in a gradient fashion 40%:60% ethyl acetate/hexanes to 60:40 ethyl acetate/hexanes to afford 3.8 g of a pure yellow oil. Yield 89%. $^1$H NMR (400 MHz, $CDCl_3$, δ): 5.93 (m, 2H), 5.77 (m, 2H), 4.14 (m, 4H), 4.05 (dq, 4H), 1.39 (d, OH, 2H); $^{13}$C NMR (400 MHz, $CDCl_3$, δ): 222.38 (C=S), 134.55 (C4), 124.39 (C3), 63.0 (C5), 38.59 (C2); MS (ESI, m/z): [M+Li]$^+$ calcd for $C_9H_{14}O_2S_3$, 257.0; found, 257.0.

Compound 7: To a solution of compound 6 (5.0 g, 19.96 mmol) in THF (220 mL) degassed under $N_2$ at 0 C was added triphenylphosphine (18.33 g, 70 eq) and acrylic acid (5.03 g, 70 mmol). To the reaction was added DEAD 40% in toluene (32 mL, 70 mmol) dropwise over 30 minutes. The reaction was allowed to warm to RT and stir overnight. The triphenylphosphine oxide salts were precipitated out with hexanes. The oil was purified by flash chromatography using 10:90 ethyl acetate/hexanes to yield 2.25 g of the trans-trans isomer. Yield 33%. $^1$H NMR (400 MHz, CDCl$_3$, δ): 6.42 (dd, 2H), 6.12 (dd, 2H), 5.86 (m, 6H), 4.63 (m, 4H, CH$_2$), 4.05 (dt, 4H, CH$_2$); $^{13}$C NMR (400 MHz, CDCl$_3$, δ): 221.94 (C=S), 165.88 (C6), 131.26 (C8), 129.26 (C7), 128.31 (C4), 127.51 (C3), 64.15 (C5), 38.43 (C2); UV-vis (methanol): λ$_{max}$ (ε)=420 nm (34000); MS (ESI, m/z): [M+Na]$^+$ calcd for C$_{15}$H$_{18}$O$_4$S$_3$, 381.0; found, 381.0.

Compound 8: The following molecule was synthesized from 4-(chloromethyl) benzyl alcohol (15 g, 96 mmol) in a solution of DCM (500 mL), whereas the concentration of the solution was 0.19M, at 0 C under N$_2$ was added imidazole (16.31 g, 239 mmol). The reaction was allowed to stir for 15 minutes. To the reaction was added TBDMSCI (18.76 g, 125 mmol). The solution was allowed to warm to room temperature overnight. After 16 hours, the reaction was filtered. The organic layer was washed with 1N HCL (100 mL), DI Water (100 mL×3), and brine (100 mL). The organic layer was dried over sodium sulfate and filtered. The product was reduced in vacuo, and the crude clear oil was purified by flash chromatography using 100% hexanes to yield 23.12 g of pure product. $^1$H NMR (400 MHz, CDCl$_3$, δ): 7.34 (m, 4H), 4.75 (s, 2H), 4.59 (s, 2H), 0.95 (s, 9H), 0.11 (s, 6H); $^{13}$C NMR (400 MHz, CDCl$_3$, δ): 141.99 (Ar—C5), 136.20 (Ar—C2), 128.66 (Ar—C3), 126.46 (Ar—C4) 64.75 (C6), 46.34 (C1), 26.10 (C9), 18.57 (C8), 5.11 (C7); MS (ESI, m/z): [M+Na]$^+$ calcd for C$_{14}$H$_{23}$ClOSi, 293.1; found, 293.1.

Compound 9: To a solution of dry Acetonitrile (100 mL=1M solution concentration) under N$_2$ and degassed for 30 minutes was added potassium carbonate (11.8 g, 85.3 mmol) and carbon disulfide (6.82 g, 89.6 mmol). The reaction was stirred vigorously for 15 minutes. To the solution was added (23.12 g, 85.3 mmol), and the reaction turned an immediate yellow color. The reaction was heated to 40 C and allowed to react for 48 hours. The reaction showed complete conversion by NMR analysis. The reaction was reduced in vacuo to yield a pure yellow solid. The yield of the reaction was quantitative in yield. $^1$H NMR (400 MHz, CDCl$_3$, δ): 7.30 (m, 8H, Ar—H), 4.73 (s, 4H), 4.62 (s, 4H), 0.96 (s, 18H), 0.11 (s, 12H); $^{13}$C NMR (400 MHz, CDCl$_3$, δ): 222.95 (C=S), 141.26 (Ar—C6), 133.49 (Ar—C3), 129.27 (Ar—C4), 126.46 (Ar—C5), 64.73 (C7), 41.49 (C2), 26.08 (C10), 18.53 (C9), 5.13 (C8); MS (ESI, m/z): [M+Na]$^+$ calcd for C$_{29}$H$_{46}$O$_2$S$_3$Si, 601.2; found, 601.2.

Compound 10: To a solution of the benzyl trithiocarbonate (22.1 g, 38.2 mmol) in DCM (550 mL) at 0 C under N$_2$ was added AcOH (8.03 g, 3.5 eq) and TBAF (114 mL, 114 mmol). The reaction was allowed to warm up to RT overnight. After 24 hrs, the reaction was ceased. The organic layer was washed with water (250 mL×2), 1N HCL, and brine (250 mL). The organic layer was dried over sodium sulfate, filtered, and reduced in vacuo to yield a crude yellow solid. The solid was purified by flash chromatography in a gradient fashion 30%: 70% ethyl acetate/hexanes to 100% ethyl acetate to afford 9.65 g of a pure yellow solid. Yield 72%. $^1$H NMR (400 MHz, DMSO-d6, δ): 7.30 (m, 8H, Ar—H), 5.18 (t, OH, 2H), 4.65 (s, 4H), 4.47 (d, 4H); $^{13}$C NMR (400 MHz, DMSO-d6, δ): 222.55 (C=S), 142.14 (C6), 133.27 (C3), 129.01 (C4), 126.769 (C5), 62.59 (C7), 40.40 (C2); MS (ESI, m/z): [M+Na]$^+$ calcd for C$_{17}$H$_{18}$O$_2$S$_3$, 373.1; found, 373.1.

Compound 11: To a solution of CRF-2-15 (5.0 g, 14.3 mmol) in THF (160 mL) degassed under N$_2$ was added triphenylphosphine (13.1 g, 49.9 mmol) and acrylic acid (3.6 g, 49.9 mmol). The reaction was cooled to 0 C and DEAD 40% in toluene (22.73 mL, 49.9 mmol) was added dropwise. After an hour the reaction was warmed to room temperature and stirred for 24 hours. The reaction was diluted with hexanes to precipitate the triphenylphosphine oxide by-product and was filtered. The crude solid was purified by flash chromatography using 80:20 ethyl acetate/hexanes to yield 6.51 g of a yellow waxy solid. Yield 99%. $^1$H NMR (400 MHz, CDCl$_3$, δ): 7.32 (m, 8H, Ar—H), 6.44 (dd, 2H), 6.15 (dd, 2H), 5.84 (dd, 2H), 5.17 (s, 4H), 4.60 (s, 4H); $^{13}$C NMR (400 MHz, CDCl$_3$, δ): 222.28 (C=S), 165.96 (C=O), 135.52 (C3), 135.16 (C6), 131.27 (C10), 129.50 (C4), 128.59 (C5), 128.22 (C9), 65.90 (C7), 41.11 (C2); UV-vis (methanol): λ$_{max}$ (ε)=430 nm (45401); MS (ESI, m/z): [M+Na]$^+$ calcd for C$_{23}$H$_{22}$O$_4$S$_3$, 481.1; found, 481.1.

Compound 12: Synthesis of 4-methoxy-4'-methylthiobiphenyl

The intermediate was synthesized by Kumada coupling of 4-bromothioanisole and 4-iodoanisole. A Grignard solution was prepared by adding Mg turnings (2.87 g, 118.2 mmol) and catalytic I$_2$ to 4-Bromothioanisole (20.0 g, 98.5 mmol) under N$_2$. The solution was gently refluxed in 200 mL of THF until only trace Mg metal was present in the reaction mixture. The solution was cooled and placed into an addition funnel under N$_2$.

To a solution of 4-iodoanisole (23.05 g, 98.5 mmol) and palladium triphenylphosphine tetrakis (1.14 g, 0.98 mmol) in 200 mL of refluxing THF under N$_2$ was added the above Grignard solution dropwise. After one hour the addition was complete and Mg salts began to crash out of the reaction solution. The solution was refluxed for an additional hour and then cooled to RT. The reaction was poured into a solution of ice and 1N HCL. The solution immediately became cloudy and a precipitate formed. The precipitate was filtered, washed with water, and dried in vacuo. The crude material was recrystallized from 1:1 Hexane/IPA to yield 16.52 g of pure compounds. Yield 78%. $^1$H NMR (400 MHz, CDCl$_3$, δ): 7.51 (m, 4H, Ar—H), 7.33 (m, 2H, Ar—H), 6.99 (m, 2H, Ar—H), 3.86 (s, 3H, OCH$_3$), 2.53 (s, 3H, SCH$_3$); $^{13}$C NMR (400 MHz, CDCl$_3$, δ): 159.21 (C2), 137.82 (C6), 136.82 (C5), 133.14 (C9), 127.93 (C8), 127.21 (C4), 127.15 (C7), 114.35 (C3), 55.43 (C1), 16.141 (C10); MS (ESI, m/z): [M+Li]$^+$ calcd for C$_{14}$H$_{14}$OS, 231.1; found, 231.1.

Compound 13: Synthesis of 4-hydroxy-4'-mercaptobiphenyl

To a solution of 4-methoxy-4'methylthiobiphenyl (16.0 g, 69.5 mmol) in 275 mL DMF under N$_2$ was added sodium thiosulfate (14.6 g, 2.5 eq). The solution was heated to a gentle reflux overnight. The solution was quenched with a solution of ice water with 50 mL of 1N HCl. The crude solid was filtered, dried, and recrystallized from 1:1: hexanes/IPA to yield 11.52 g of product. 81.9% yield. $^1$H NMR (400 MHz, CDCl$_3$, δ): 7.48 (m, 4H, Ar—CH), 7.32 (m, 2H, Ar—CH), 6.88 (m, 2H, Ar—CH), 2.50 (s, 2H); $^{13}$C NMR (400 MHz, CDCl$_3$, δ): 157.6 (C1), 138.9 (C5), 138.4 (C4), 133.7 (C8), 130.3 (C7), 128.7 (C3), 127.7 (C6), 114.3 (C2), 55.4 (C9), 16.1 (C10); MS (ESI, m/z): [M−H]$^-$ calcd for C$_{12}$H$_{10}$OS, 201.0; found, 201.0.

Compound 14: Synthesis of the Biphenyl Allyl Sulfide

To a solution of MeOH at 0 C under N$_2$ was added Na metal (1.03 g, 45 mmol). The solution was slowly allowed to warm to room temperature. 4-hydroxy-4'mercaptobiphenyl (8.0 g, 40 mmol) was added to the reaction, and the reaction was heated to reflux. 3-chloro-2-chloromethyl propene (2.25 g, 18 mmol) was added dropwise over an hour, and the reaction was allowed to reflux overnight. The solution was reduced in vacuo and purified by flash chromatography 20:80 acetone/ hexanes to yield 3.92 g of the pure allyl sulfide. Yield 47.7%. $^1$H NMR (400 MHz, DMSO-d6, δ): 9.56 (s, 2H, Ar—OH), 7.46 (m, 8H, Ar—H), 7.33 (m, 4H, Ar—H), 6.82 (m, 4H, Ar—H), 5.06 (s, 2H, C=CH$_2$), 3.8 (s, 4H); $^{13}$C NMR (400 MHz, DMSO-d6, δ): 157.13 (C1), 139.57 (C10), 137.92 (C5), 133.15 (C8), 129.97 (C4), 129.52 (C7), 127.43 (C3), 126.24 (C6), 116.55 (C11), 115.71 (C2) 36.89 (C9); MS (ESI, m/z): [M−H]$^−$ calcd for C$_{28}$H$_{24}$O$_2$S$_2$, 455.1; found, 455.1.

Compound 15: Synthesis of the Biphenyl Allyl Sulfide Diacrylate

To a solution of the Biphenyl Allyl Sulphide (3.5 g, 7.67 mmol) in 77 mL of THF at 0 C under N$_2$ was added triethylamine (2.67 mL, 2.5 eq). The solution was stirred for 5 minutes and then acryloyl chloride (1.55 mL, 2.5 eq) was added dropwise. The solution was allowed to warm to room temperature and stir overnight. The solution was filtered and reduced in vacuo to a crude solid. The solid was purified by flash chromatography to yield 1.82 g. Yield 42%. $^1$H NMR (400 MHz, Acetone d-6, δ): 7.66 (m, 4H, Ar—H), 7.58 (m, 2H, Ar—H), 7.43 (m, 2H, Ar—H), 7.24 (m, 2H, Ar—H), 6.57 (dd, 2H), 6.39 (dd, 2H), 6.10 (dd, 2H), 5.12 (s, 2H), 3.88 (s, 4H); $^{13}$C NMR (400 MHz, Acetone d-6, δ): 165.05 (C3), 151.47 (C4), 141.16 (C13), 138.91 (C8), 138.80 (C7), 136.49 (C11), 133.29 (C1), 130.91 (C10), 129.04 (C2), 128.65 (C6), 128.28 (C9), 123.20 (C5), 117.39 (C14), 38.48 (C12); MS (ESI, m/z): [M+Na]$^+$ calcd for C$_{34}$H$_{28}$O$_4$S$_2$, 587.10; found, 587.10.

Compound 16: Synthesis of MBH

The allyl sulfides were synthesized as follows. To a 1 L flask at 0 C was added 600 mL of methanol. The solution was kept under 30 C as Na metal (19 g, 0.83 mol) was added in small portions. After all the sodium had reacted, 2-mercaptoethanol (57.8 g, 2.2 eq) was added to the solution of sodium methoxide. The solution was heated to reflux and 3-chloro-2-chloromethyl-1-propene (42 g, 1 eq) was added dropwise over 1 hour. The solution was allowed to reflux overnight. The solution was cooled to 25 C, filtered, and reduced in vacuo to remove the methanol. The crude material was taken up in 500 mL's of water and extracted with ether (4×150 mL). The ether layer was washed with brine and dried over sodium sulfate. The organic layer was reduced in vacuo. The crude light-yellow oil was purified by vacuum distillation to yield 65 g of the MBH. Yield 92.3%. $^1$H NMR (400 MHz, CDCl$_3$, δ): 5.00 (s, 2H), 3.68 (t, 4H), 3.29 (s, 4H), 2.67 (s, OH, 2H), 2.61 (t, 4H); $^{13}$C NMR (400 MHz, CDCl$_3$, δ): 140.31 (C=CH$_2$), 116.14 (C5), 60.31 (C1), 34.85 (C3), 33.55 (C2).

Compound 17: Synthesis of MBTMA

To MBH (50 g, 1 eq) under N$_2$ at 0 C was added freshly distilled methylene chloride and triethylamine (53.42 g, 2.2 eq). After 30 minutes of degassing with N$_2$, acryloyl chloride (40 mL, 47.78 g, 2.2 eq) was added dropwise over 3 hours. The reaction was warmed to 25 C and allowed to stir overnight. The organic layer was washed with water, brine, and dried over magnesium sulfate. The organic layer was filtered and reduced in vacuo to a brownish-yellow crude oil. The oil was purified by flash chromatography 70:30 hexanes/ethyl acetate to yield an off-colored oil 46 g. Yield 60.5%. $^1$H NMR (400 MHz, CDCl$_3$, δ): 6.40 (dd, 2H), 6.10 (dd, 2H), 5.83 (dd, 2H), 5.04 (s, 2H), 4.26 (t, 4H), 3.32 (s, 4H), 2.67 (t, 4H); $^{13}$C NMR (400 MHz, CDCl$_3$, δ): 166.03 (C=O), 140.40 (C7), 131.39 (C1), 128.35 (C2), 116.85 (C8), 63.33 (C4), 35.47 (C6), 29.41 (C7).

Compound 18: Synthesis of Phenyl Allyl Sulfide

To a 1 L flask at 0 C was added 160 mL of methanol. The solution was kept under 30 C as Na metal (5.10 g, 221.24 mmol) was added in small portions. After all the sodium had reacted, 4-hydroxythiophenol (25.0 g, 2.2 eq) was added to the solution of sodium methoxide. The solution was heated to reflux and 3-chloro-2-chloromethyl-1-propene (11.26 g, 1 eq) was added dropwise over 1 hour. The solution was allowed to reflux overnight. The solution was cooled to 25 C, filtered, and reduced in vacuo to remove the methanol. The crude material was taken up in 500 mL of water and extracted with ether (4×150 mL). The ether layer was washed with 1N HCl, water, brine, and dried over sodium sulfate. The organic layer was reduced in vacuo to a crude orange oil. The oil was purified by flash chromatography 90:10 hexanes/ethyl acetate to yield 23.52 g of a colorless oil. Yield 85.8%. $^1$H NMR (400 MHz, CDCl$_3$, δ): 7.23 (m, 4H, Ar—H), 6.74 (m, 4H, Ar—H), 5.84 (s, 2H, Ar—OH), 4.70 (s, 2H, C=CH$_2$), 3.57 (s, 4H, CH$_2$); $^{13}$C NMR (400 MHz, CDCl$_3$, δ): 155.3 (C1), 140.45 (C10), 138.6 (C5), 134.3 (C8), 132.7 (C4), 126.0 (C7), 116.5 (C3), 116.0 (C6), 40.63 (C11); MS (ESI, m/z): [M+Li]$^+$ calcd for C$_{16}$H$_{16}$O$_2$S$_2$, 344.3; found, 344.3.

Compound 19: Phenyl Allyl Sulfide Diacrylate

To compound 18 (23.52 g, 1 eq) under N$_2$ at 0 C was added freshly distilled methylene chloride and triethylamine (17.2 g, 2.2 eq). After 30 minutes of degassing with N$_2$, acryloyl chloride (15.38 g, 2.2 eq) was added dropwise over 1 hours. The reaction was warmed to 25 C and allowed to stir overnight. The organic layer was washed with 1N HCl, sodium bicarbonate, water, brine, and dried over magnesium sulfate. The organic layer was filtered and reduced in vacuo to an orange oil. The oil was purified by flash chromatography 95:5 hexanes/ethyl acetate going to 90:10 hexanes/ethyl acetate to yield an off-colored oil 12.82 g. Yield 40.2%. $^1$H NMR (400 MHz, CDCl$_3$, δ): 7.35 (m, 4H, Ar—H), 7.06 (m, 4H, Ar—H), 6.59 (dd, 2H), 6.30 (dd, 2H), 6.00 (dd, 2H), 4.91 (s, 2H), 3.69 (s, 4H); $^{13}$C NMR (400 MHz, CDCl$_3$, δ): 164.29 (C=O), 149.44 (C4), 139.65 (C9), 133.02 (C1), 132.72 (C6), 131.75 (C2), 127.82 (C5), 122.01 (C10), 39.17 (C9); MS (ESI, m/z): [M+Na]$^+$ calcd for C$_{22}$H$_{20}$O$_4$S$_2$, 435.04; found, 435.04.

Compound 20: Matyjaszewski Trithiocarbonate

The compound was synthesized from a literature procedure [8]. The flask was charged with S,S'-bis(α,α'-dimethyl-α"-acetic acid)-trithio-carbonate (2.78 g, 9.8 mmol) and triphenylphosphine (9.03 g, 34.5 mmol) and subsequently deoxygenated by purging with nitrogen for 30 min. 2-Hydroxyethyl methacrylate (4.48 g, 34.5 mmol) and anhydrous tetrahydrofuran (110 mL) were added. The flask was immersed in an ice bath, and cooled to 0 C. A solution of diethyl azodicarboxylate (15.7 mL, 34.5 mmol) was added dropwise. The reaction was warmed to RT and stirred for 16 hours. The reaction was diluted with hexanes and the triphenylphosphine oxide salts were filtered off. The filtrate was reduced in vacuo to a crude red oil. The oil was purified by flash chromatography 90:10 hexanes/ethyl acetate to yield 2.8 g of the trithiocarbonate. Yield 56%. $^1$H NMR (400 MHz, CDCl$_3$, δ): 6.11 (dd, 2H), 5.57 (dd, 2H), 4.33 (s, 8H), 1.93 (s, 6H), 1.63 (s, 12H); $^{13}$C NMR (400 MHz, CDCl$_3$, δ): 218.45 (C=S), 172.41 (C7), 166.97 (C4), 135.90 (C2), 126.03 (C1), 63.49 (C6), 62.06 (C5), 56.05 (C8), 25.05 (C9), 18.25 (C3); MS (ESI, m/z): [M+Na]$^+$ calcd for C$_{21}$H$_{30}$O$_8$S$_3$, 529.1; found, 529.1.

References
1. B. Giese, Radicals in organic synthesis: formation of carbon-carbon bonds, Pergamon Press, Oxford (1986)
2. W. B. Motherwell, D. Crich, Free radical chain reactions in organic synthesis, Academic Press, London (1992)
3. Moad, G., Rizzardo, E., & Thang, S. H. (2008). Radical addition-fragmentation chemistry in polymer synthesis. *Polymer,* 49(5), 1079-113
4. G. F. Meijs, E. Rizzardo, Die Makromol Chem Rapid Commun, 9 (1988), pp. 547-551.

5. G. F. Meijs, E. Rizzardo, S. H. Thang, Macromolecules, 21 (1988), pp. 3122-3124
6. P. Cacioli, D. G. Hawthorne, R. L. Laslett, E. Rizzardo, D. H. Solomon, J Macromol Sci Chem, A23 (1986), pp. 839-852.
7. Chiefari, J.; Y. K. Chong, F. Ercole, J. Krstina, J. Jeffery, T. P. T. Le, R. T. A. Mayadunne, G. F. Meijs, C. L. Moad, G. Moad, E. Rizzardo, H. Thang (1998), "Living Free-Radical Polymerization by Reversible Addition-Fragmentation Chain Transfer: The RAFT Process". *Macromolecules* 31 (16): 5559-5562.
8. Lai, J., & Filla, D. (2002). Functional polymers from novel carboxyl-terminated trithiocarbonates as highly efficient RAFT agents. *Macromolecules*, 6754-6756.
9. Nicolaÿ, R., Kamada, J., Van Wassen, A., & Matyjaszewski, K. (2010). Responsive Gels Based on a Dynamic Covalent Trithiocarbonate Cross-Linker. *Macromolecules*, 43(9), 4355-4361.
10. Kloxin, C. J., Scott, T. F., Park, H. Y., & Bowman, C. N. (2011). Mechanophotopatterning on a photoresponsive elastomer. *Advanced materials* 23(17), 1977-81.
11. Davidson, C L; Feilzer, A J. *Journal of Dentistry.* 1997, 25, 435.
12. Braga, R; et al. *Dental Materials.* 2005, 21, 962.
13. Park, H. Y., Kloxin, C. J., Scott, T. F., & Bowman, C. N. (2010). Covalent adaptable networks as dental restorative resins: stress relaxation by addition-fragmentation chain transfer in allyl sulfide-containing resins. *Dental materials: official publication of the Academy of Dental Materials,* 26(10), 1010-6. The Academy of Dental Materials.
14. Park, H. Y., Kloxin, C. J., Scott, T. F., & Bowman, C. N. (2010). Stress Relaxation by Addition—Fragmentation Chain Transfer in Highly Crosslinked Thiol-Yne Networks. *Macromolecules,* 43(24), 10188-10190
15. Kloxin, C. J., Scott, T. F., & Bowman, C. N. (2009). Stress relaxation via addition-fragmentation chain transfer in a thiol-ene photopolymerization. *Macromolecules,* 42(7), 2551-2556.
16. Diana Leung, Christopher N. Bowman (2011). "Reducing Shrinkage Stress of Dimethacrylate Networks by Reversible Addition-Fragmentation Chain Transfer" *Macromolecular Chemistry and Physics Volume* 213, Issue 2, 198-204.
17. Scott, T. F., Schneider, A. D., Cook, W. D., & Bowman, C. N. (2005). Photoinduced plasticity in cross-linked polymers. *Science.* 308(5728), 1615-7. 1194.
18. Moad, G.; E. Rizzardo; S. H. Thang (2008). "Radical addition-fragmentation chemistry in polymer synthesis". Polymer 49 (5): 1079-1131.
19. Moad, G., & Rizzardo, E. (2009). "Living Radical Polymerization by the RAFT Process—A Second Update." Australian Journal of Chemistry, 1402-1472.
20. Aoyagi, N., Ochiai, B., Mori, H., & Endo, T. (2006). Mild and Efficient One-Step Synthesis of Trithiocarbonates Using Minimum Amount of CS 2. *Synlett*, (4), 0636-0638.
21. Aoyagi, N., & Endo, T. (2009). Functional RAFT agents for radical-controlled polymerization: Quantitative synthesis of trithiocarbonates containing functional groups as RAFT agents using equivalent amount of CS 2. *Journal of Polymer Science Part A: Polymer Chemistry,* 47(14), 3702-37093).
22. Lai, J. T., Filla, D., & Shea, R. (2002). Functional Polymers from Novel Carboxyl-Terminated Trithiocarbonates as Highly Efficient RAFT Agents. *Tetrahedron,* 6754-6756.
23. M. H. Stenzel, in Handbook of RAFT Polymerization (Ed. C. Barner-Kowollik) 2008, pp. 315-372 (Wiley-VCH:Weinheim).
24. L. Barner, T. P. Davis, M. H. Stenzel, C. Barner-Kowollik, Macromol. Rapid Commun. 2007,28,539.
25. Park, H. Y., Kloxin, C. J., Abuelyaman, A. S., Oxman, J. D., & Bowman, C. N. (2012). Stress Relaxation via Addition-Fragmentation Chain Transfer in High T. *Macromolecules* 2012, 45, 5640-5646.
26. F. Duus, in Comprehensive Organic Chemistry, ed. D. Barton and W. D. Ollis, Pergamon, New York, 1979, vol. 3, p. 342; M. Bogemann, S. Peterson, O. E. Schultz and H. Soll, in Methoden der organischen chemie, ed. E. Muller, Houben-Weyl, Berlin, 1955, vol. 9, p. 804.
27. H. C. Godt and A. E. Wanns, J. Org. Chem., 1961, 26, 4047 and refs therein.
28. Perrier, S.; Takolpuckdee, P J. Polym. Sci., Part A: Polym. Chem. 2005, 43, 5347-5393.
29. *Comprehensive Organic Chemistry*; Barton, D., Ollis, W. D., Eds.; Pergamon Press Ltd, Oxford, UK, 1979, Vol. 3, 434-436, 456.
30. A. Sugawara, M. Shirahata, S. Sato and R. Sato, Bull. Chem. Soc. Jpn., 1984, 57, 3353
31. Devdutt Chaturvedi, Amit K. Chaturvedi, Nisha Mishra, Virendra Mishra, An efficient, one-pot synthesis of trithiocarbonates from the corresponding thiols using the Mitsunobu reagent *Tetrahedron Letters*, Volume 49, Issue 33, 11 Aug. 2008, Pages 4886-4888.
32. Lee, A. W. M.; Chan, W. H.; Wong, H. C. Synth. Commun. 1988, 18, 1531.
33. Capperu, A., Boninf, B. F., Zad, P., Organica, C., & Capponi, G. (1994). Thiophilic Allylation of Dithioesters and Trithiocarbonates, 35(1), 161-164.
34. U.S. Pat. No. 7,943,680 to Bowman et al.

What is claimed is:

1. A monomer having a structure C-B-A-B-C, the monomer comprising:
   (a) core unit A, wherein the core unit is trithiocarbonate;
   (b) linker units B connected to the core unit;
      wherein the linker units have a first portion B and a second portion B;
      wherein the first portion is connected to the core unit, and wherein the first portion is selected from the group consisting of
         (i) unbranched C2-C10 alkanes;
         (ii) a branched C2-C10 alkane, wherein at least one branch of the alkane is one of the following groups: a cyano (CN) group, a nitro ($NO_2$) group, a trihalide, a carboxylic acid, a sulfonate, an ester, a ketone, and an aldehyde;
         (iii) C2-C10 alkenes;
         (iv) C2-C10 alkynes; and
         (v) aromatic rings;
      wherein the second portion is an oxygen atom connected to an end of the first portion; and
   (c) end units C connected to the oxygen atoms of the linker units, wherein the end units are selected from the group consisting of hydrogen, acrylates, and methacrylates.

2. The monomer of claim 1, wherein the first portion B of the linker units are C2-C10 alkanes, and wherein the end units C are acrylates.

3. The monomer of claim 2, having the below chemical structure:

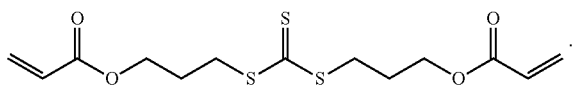 [SMILES: C=CC(=O)OCCCSC(=S)SCCCOC(=O)C=C]

4. The monomer of claim 1, wherein the first portion B of the linker units are C2-C10 alkenes, and wherein the end units C are acrylates.

5. The monomer of claim 4, having the below chemical structure:

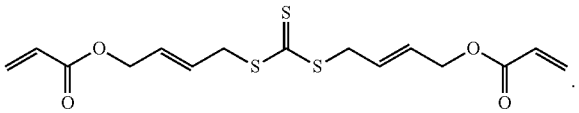 [SMILES: C=CC(=O)OC/C=C/CSC(=S)SC/C=C/COC(=O)C=C]

6. The monomer of claim 1, wherein the first portion B of the linker units are benzylic groups, and wherein the end units C are acrylates.

7. The monomer of clam 6, having the below chemical structure:

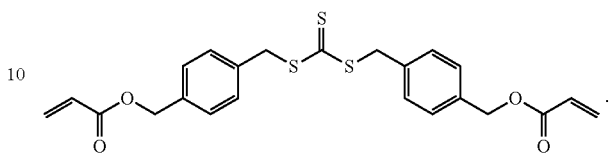

8. The monomer of claim 1, wherein the aromatic rings are selected from the group cosisting of benzylic groups, phenyl groups, and diphenyl groups.

* * * * *